United States Patent [19]
Fukuda et al.

[11] Patent Number: 5,766,910
[45] Date of Patent: Jun. 16, 1998

[54] EXPRESSION OF THE DEVELOPMENTAL I ANTIGEN BY A CLONED HUMAN CDNA ENCODING A MEMBER OF A BETA-1, 6-N-ACETYLGLUCOSAMINYLTRANSFRASE GENE FAMILY

[75] Inventors: Minoru Fukuda, San Diego, Calif.; Marti F. A. Bierhuizen, Schiedam, Netherlands

[73] Assignee: La Jolla Cancer Research Foundation, La Jolla, Calif.

[21] Appl. No.: 488,135

[22] Filed: Jun. 7, 1995

Related U.S. Application Data

[62] Division of Ser. No. 118,906, Sep. 9, 1993, Pat. No. 5,484,590.
[51] Int. Cl.$^6$ .......................... C12N 15/54; C12N 9/10; C12N 5/10; C12N 15/63
[52] U.S. Cl. .............. 435/193; 435/70.3; 435/172.3; 435/325; 435/358; 435/252.3; 435/320.1; 536/23.1; 536/23.2; 935/14; 935/22; 935/27; 935/66
[58] Field of Search .......................... 435/193, 70.3, 435/172.3, 240.2, 252.3, 320.1, 325, 358; 536/23.1, 23.2; 935/14, 22, 27, 66

[56] References Cited

U.S. PATENT DOCUMENTS 5,032,519  7/1991  Paulson et al. .................... 435/193
5,324,663  6/1994  Lowe .................................. 435/320.1

OTHER PUBLICATIONS

Schachater, Harry "Condensation of Research" *Chemtracts–Biochemistry and Molecular Biology* 4:164–167 (1993).

Joziasse, D. H. "Mammalian Glycosyltransferases: Genomic Organization and Protein Structure." *Glycobiol.* 2:271–277 (1992).

Paulson, J.C. and Colley, K.J. "Glycosyltransferases, Structure, Localization and Control of Cell Type–Specific Glycosylation." *J. Biol. Chem.* 264:17615–17618 (1989).

Schachter, H. "Enzymes Associated With Glycosylation." *Curr. Opinion Struct. Biol.* 1:755–765 (1991).

Smith, D.F. et al., "Transfer and Expression of a Murine UDP–Gal:β–D–Gal–α1,3–galactosylatransferase in Chinese Hamster Ovary Cells." *J. Biol. Chem.* 265:6225–6235 (1990).

Gu, Jianguo et al. "Deficiency of β1–6 N–Acetylglucosaminyltransferase Involved in the Biosynthesis of Blood Group I Antigen in the Liver of LEC Rats." *Jpn. J. Cancer Res.* 83:878–884 (1992).

Bierhuizen, Marti F.A. and Fukuda, Minoru. "Expression Cloning of a cDNA Encoding UDP–GlcNAc:Galβ1–3–GalNAc–R (GlcNAc to GalNAc) β1–6GlcNAc Transferase by Gene Transfer Into CHO Cells Expressing Polyoma Large Tumor Antigen." *Proc. Natl. Acad. Sci. USA* 89:9326–9330 (1992).

Piller, Friedrich et al., "Biosynthesis of Blood Group I Antigens." *J. Biol. Chem.* 259:13385–13390 (1984).

Zielenski, Julian and Koscielak, Jerzy, "Sera of i Subjects Have the Capacity to Synthesize the Branched GlcNAcβ(1→6) [GlcNAc(β1→3)] Gal . . . Structure." *FEBS.* 163:114–118 (1983).

Bierhuizen, Marti F.A. et al. "Expression of the Developmental I Antigen by a Cloned Human cDNA Encoding a Member of a β–1, 6–N–Acetylglucosaminyltransferase Gene Family." *Genes and Development.* 7:468–478 (1993).

*Primary Examiner*—Rebecca E. Prouty
*Attorney, Agent, or Firm*—Campbell & Flores LLP

[57] ABSTRACT

The present invention provides an isolated nucleic acid molecule encoding both a soluble and membrane-bound human β-1,6-N-acetylglucosaminyltransferase, the I-branching enzyme (IGnT). The invention also provides vectors containing the isolated nucleic acid molecule encoding human IGnT as well as recombinant host cells transformed with the vectors. The invention further provides a method of preparing a membrane-bound form of human IGnT and methods of preparing and purifying soluble human IGnT and active fragments of either form. Also provided are antisense oligonucleotides complementary to a nucleic acid molecule encoding a human IGnT or an active fragment thereof, antibodies directed to the human IGnT, pharmaceutical compositions related to the human IGnT and transgenic nonhuman mammals expressing DNA encoding normal or mutant human IGnT. Also provided are methods for regulating the expression of human IGnT and methods for modifying a biological function mediated by the regulatory activity of human IGnT. Methods of detecting the presence of linear polylactosaminoglycans expressing i antigenic determinants on a cell surface also are provided.

10 Claims, 12 Drawing Sheets

```
A
 1      TAC ATC ACA GCC CCT TTA TCT AAG GAA GAA GCT GAC TTT CCC TTG GCA TAT ATA ATG GTC ATC CAT   306
C2      --T --T GT- -AA --C C-T AG- --A --- --G --- --A A-A --- --- --A --- TCT --A --G G-T ---   390
1-P     Tyr Ile Thr Ala Pro Leu Ser Lys Glu Glu Ala Asp Phe Pro Leu Ala Tyr Ile Met Val Ile His   102
C2-P    --- Val Glu --- --- --- --- --- --- --- --- Glu --- --- --- --- Ser Ile --- --- Val ---   130

1      CAT CAC TTT GAC ACC TTT GCA AGG CTC TTC AGG GCT ATT TAC ATG CCC CAA AAT ATC TAC TGT GTT   374
C2      --C A-G A-- --A -TG C-- -AC --- --G C-G --- -C --T --- --T --G --- T-- --T --C ---   456
1-P     His His Phe Asp Thr Phe Ala Arg Leu Phe Arg Ala Ile Tyr Met Pro Gln Asn Ile Tyr Cys Val   124
C2-P    --- --- --- --- --- Lys Ile Glu Met Leu Asp --- --- --- --- Leu --- --- --- --- Phe ---   152

1      CAT GTG GAT GAA AAA GCA ACA ACT GAA TTT AAA GAT GCG GTA GAG CAA CTA TTA AGC TGC TTC CCA   438
C2      --- --- --- --C AC- --- T-C GAG GA- TCC -A- TT- -C- --A --G AT- GGC A-C GCT TC- -GT --T AGT   522
1-P     His Val Asp Glu Lys Ala Thr Thr Glu Phe Lys Asp Ala Val Glu Gln Leu Leu Ser Cys Phe Pro   146
C2-P    --- --- --- --- Thr --- Ser Glu Asp Ser Tyr Leu Ala --- --- Met Gly Ile Ala --- --- Ser   174
```

FIG. 3A

```
I      AAC GCT TTT CTG GCT TCC AAG ATG GAA CCC GTT GTC TAT GGA GGG ATC TCC AGG CTC CAG GCT GAC    504
C2     --T -TC --- G-- --C AG- CGA T-- --G AGT --G --T --- -C- TC- TGG AG- C-- G-T --- --- ---    588
I-P    Asn Ala Phe Leu Ala Ser Lys Met Glu Pro Val Val Tyr Gly Gly Ile Ser Arg Leu Gln Ala Asp    168
C2-P   --- Val --- Val --- --- Arg Leu --- Ser --- --- --- --- --- Ala Ser Trp --- --- Val ---    196

I      CTG AAC TGC ATC AGA GAT CTT TCT GCC TTC GAG GTC TCA TGG AAG TAC GTT ATC AAC ACC TGT GGG    570
C2     --C --- --- --- -AG --- --C --A A-G AGT -CA AAC --- --- --- --- T-G --A --T CTT --T        654
I-P    Leu Asn Cys Ile Arg Asp Leu Ser Ala Phe Glu Val Ser Trp Lys Tyr Val Ile Asn Thr Cys Gly    190
C2-P   --- --- --- --- Met Lys --- --- Tyr --- Met Ser Ala Asn --- --- Leu --- --- --- Leu ---    218

I      CAA GAC TTC CCC CTG AAA ACC AAC AAG GAA ATA GTT CAG TAT CTG AAA                             618
C2     ATG --T -T --- A-T --- CTA --- -T --C AG- A-G --C --G                                      702
I-P    Gln Asp Phe Pro Leu Lys Thr Asn Lys Glu Ile Val Gln Tyr Leu Lys                            206
C2-P   Met --- --- --- Ile --- Leu --- --- --- --- --- --- --- Arg Lys                           234
```

```
B
1    TTG CTC CAG TGG TCC AAG GAC ACT TTC AGT CCT GAT GAG CAT TTC TGG GTG ACA CTC AAT AGG ATT    909
C2   --- A-G G-- --- G-A C-A --- --A -A- --C --- --- T-- C-- --- -CC --- C-A --- C-A --- ---    981
1-P  Leu Leu Gln Trp Ser Lys Asp Thr Phe Ser Pro Asp Glu His Phe Trp Val Thr Leu Asn Arg Ile    303
C2-P --- Met Glu --- --- Ala Gln --- --- Tyr --- --- --- --- --- --- --- Tyr --- Ala --- Ile Gln    327

1    CCA GGT GTT CCT GGC TCT ATG CCA AAT GCA TCC    948
C2   --T -AA --C --G --- --A C-C -T- --C AG- ---    1017
1-P  Pro Gly Val Pro Gly Ser Met Pro Asn Ala Ser    316
C2-P --- Glu --- --- --- --- Leu --- --- --- ---    339

C
1    TGT ATC TAT GGA AAC GGA GAC TTA AAG TGG CTG GTT AAT TCA CCA AGC CTG TTT GCT AAC AAG TTT    1098
C2   --C --T -TC --- GCT --- --G --C --- A-- C-G CGC AA- -AC CA- T-- --- --C CA- --T --- ---    1206
1-P  Cys Ile Tyr Gly Asn Gly Asp Leu Lys Trp Leu Val Asn Ser Pro Ser Leu Phe Ala Asn Lys Phe    366
C2-P --- --- Phe --- Ala --- --- Asn --- Met Leu Arg Lys His His --- --- --- --- --- --- ---    402
```

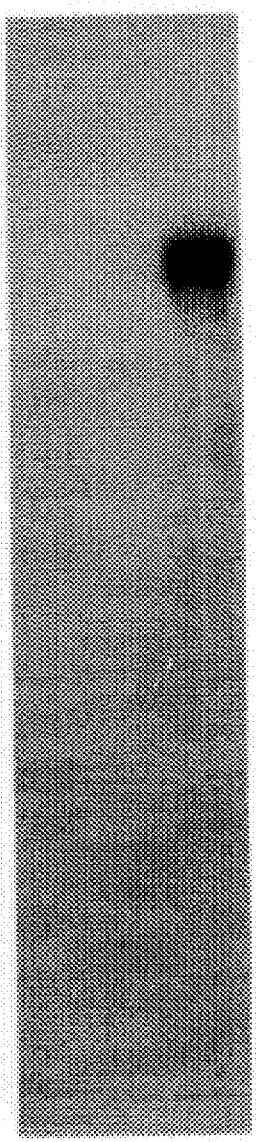

US 5,766,910

EXPRESSION OF THE DEVELOPMENTAL I ANTIGEN BY A CLONED HUMAN CDNA ENCODING A MEMBER OF A BETA-1, 6-N-ACETYLGLUCOSAMINYLTRANSFRASE GENE FAMILY

This application is a divisional of application Ser. No. 08/118,906, filed Sept. 9, 1993 now U.S. Pat. No. 5,484,590.

This invention was made in part with Government support under Grant Nos. CA33895 and CA33000, from the National Cancer Institute. The Government may have certain rights in this invention.

BACKGROUND OF THE INVENTION

Glycoconjugates are major components of the outer surface of mammalian cells. During mammalian development, the carbohydrate structures of these glycoconjugates change dramatically. In many cases, specific sets of carbohydrates are characteristic for particular stages of differentiation. Where these specific carbohydrates are recognized by specific antibodies, the carbohydrate structures are useful as differentiation antigens (Feizi, Nature 314:51–55, (1985); Fukuda et al., J. Biol. Chem., 260:6623–6631 (1985), each of which is incorporated herein by reference). In the mature organism, expression of distinct carbohydrates ultimately is restricted to specific cell types and aberrations in the specific cell surface carbohydrates often are associated with malignant transformation of the cells (Hakomori, Ann. Rev. Immunol., 2:10–126 (1984)). Although the functional significance of alterations in cell surface carbohydrates during cell differentiation and in malignancy is not completely understood, several reports suggest that these molecules are involved in the modulation of adhesive processes.

It has been generally accepted that each glycosyltransferase catalyzes a single enzymatic reaction to form a specific linkage. One notable exception is the Lewis fucosyltransferase, which can synthesize both α1,3 and α1,4 linkages (Prieels et al., J. Biol. Chem. 256:10456–10463 (1981); Kukowska-Latallo et al., Genes & Devel. 4:1288–1303 (1990), each of which is incorporated herein by reference). A specific linkage usually is associated with the formation of specific oligosaccharides, which also may contain other linkages formed in conjunction with the action of other glycosyltransferases. Thus, the presence of specific oligosaccharides on the cell surface is the result of the coordinate expression of one or more glycosyltransferase genes responsible for synthesis of the oligosaccharide linkages. Recently, cDNAs encoding approximately a dozen different glycosyltransferases have been isolated (Paulson and Colley, J. Biol. Chem., 264:17615–17618 (1989); Schachter, Curr. Opin. Struct. Biol., 1:755–765 (1991); Joziasse, Glycobiology 2:271–277 (1992)). However, little is known about the regulation of glycosyltransferases or glycosyltransferase gene expression during development and in malignancy.

Thus a need exists to identify and characterize members of the glycosyltransferase enzyme family. The present invention satisfies this need and provides related advantages as well.

SUMMARY OF THE INVENTION

The present invention provides an isolated nucleic acid molecule encoding both soluble and membrane-bound forms of human β-1,6-N-acetylglucosaminyltransferase, the I-branching enzyme (IGnT). The invention also provides vectors containing an isolated nucleic acid molecule encoding human IGnT as well as recombinant host cells transformed with such vectors. The invention further provides a method of preparing and purifying soluble human IGnT.

The present invention also provides antisense oligonucleotides complementary to a nucleic acid molecule encoding a human IGnT, antibodies directed to a human IGnT, pharmaceutical compositions related to human IGnT and transgenic nonhuman mammals that express DNA sequences encoding normal or mutant human IGnT or that express antisense oligonucleotides complementary to a DNA sequence encoding normal or mutant human IGnT. Also provided are methods for regulating the expression of human IGnT and for modifying a biological function mediated by the regulatory activity of IGnT. Methods for detecting the presence of linear polylactosaminoglycans expressing i antigenic determinants on the cell surface also are provided.

BRIEF DESCRIPTION OF THE FIGURES

FIG. 3 indicates regions in IGnT and C2GnT that exhibit a high homology with each other. I (SEQ ID NO. 1) and C2 (SEQ ID NO. 3) designate nucleotide sequences and I-P (SEQ ID NO. 2) and C2-P (SEQ ID NO. 4) designate amino acid sequences of IGnT and C2GnT, respectively. The residues are numbered with respect to the translation initiation site. Identical residues are indicated by dashes. Non-identical but similar amino acids are denoted by dots.

FIG. 4 indicates a region of modest homology between IGnT and C2GnT. I (SEQ ID NO. 5), C2 (SEQ ID NO. 7), I-P (SEQ ID NO. 6) and C2-P (SEQ ID NO. 8) are as described in the legend to FIG. 3. Residues are numbered with respect to the translation initiation site. Identical residues are indicated by dashes. Non-identical but similar amino acids are denoted by dots.

FIG. 5 indicates a region of modest homology between IGnT and C2GnT. I (SEQ ID NO. 9), C2 (SEQ ID NO. 10), I-P (SEQ ID NO. 11) and C2-P (SEQ ID NO. 12) are as described in the legend to FIG. 3. The residues are numbered with respect to the translation initiation site. Identical residues are indicated by dashes. Non-identical but similar amino acids are denoted by dots.

FIG. 6 lists the full-length DNA sequence (SEQ ID NO. 13) and deduced amino acid sequence (SEQ ID NO. 14) of IGnT. The signal/membrane-anchoring domain is doubly underlined. Potential N-glycosylation sites are marked by asterisks. The sequences are numbered relative to the translation initiation site.

FIG. 8 shows a Northern blot analysis of IGnT mRNA. Each lane contained 12 μg of poly (A)$^+$ RNA from CHO-Py-leu (lane 1), HL-60 promyelocytic (lane 2) or PA-1 teratocarcinoma (lane 3) cells. A $^{32}$P-labeled IGnT cDNA fragment representing the complete, putative lumenal domain of IGnT was used as a probe. As shown, only PA-1 cells express the IGnT mRNA. The migration positions of the RNA size markers are indicated at the left.

DETAILED DESCRIPTION OF THE INVENTION

The blood group i/I antigens were the first identified alloantigens to display a dramatic change during human development. The i antigen is expressed on erythrocytes of the fetus and neonate, but is replaced by the I antigen on erythrocytes in the majority of adults.

During mouse embryogenesis, the I antigen is expressed throughout the preimplantation period; the i antigen is first detected in the 5-day embryo. Expression of the i antigen is more pronounced in the primary endoderm and the increase in i antigen is associated with a decrease in the I antigen. The determinants that define the i and I antigens have been characterized and are carried by linear and branched polylactosaminoglycans, respectively.

Figure 1:
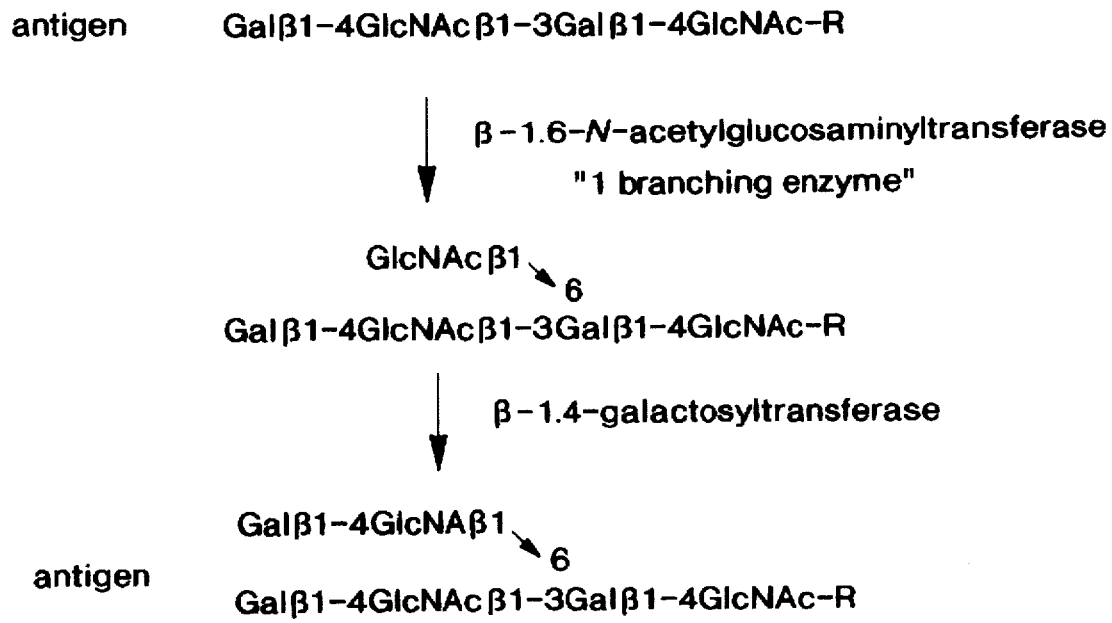
FIG. 1 depicts the structure and biosynthesis of i and I antigens. The i antigen is expressed by a linear polylactosaminoglycan and is converted into the I antigen by the stepwise addition of GlcNAcβ1→6 and Galβ1→4 residues to produce poly-N-acetyllactosamines (also called polylactosaminoglycans).

Polylactosaminoglycans are composed of repeats of N-acetyllactosamine (Galβ1→4GlcNAcβ1→3). Conversion of the i antigen to the I antigen is due to the expression of a β-1,6-N-acetylglucosaminyltransferase, the I branching enzyme (IGnT) (see FIG. 1). These polylactosaminoglycans often are modified to provide cell-type specific oligosaccharide structures. One of these structures, sialyl Le$^x$ or NeuNAcα2→3Galβ1→4(Fucα1→3) GlcNAc→R, is a ligand for the E- and P-selectins and, thus, has a critical role in the adhesion of leukocytes to endothelial cells and platelets.

Another example of a polylactosaminoglycan is the stage-specific embryonic antigen, SSEA-1. This antigen is expressed at the eight-cell stage of mouse embryonic development, after which it is restricted to specific cell types during later stages of murine development. The SSEA-1 molecule is a fucosylated oligosaccharide in which fucose is attached through α1,3-linkage to N-acetyllactosamine, forming Galβ1→4(Fucα1→3)GlcNAc→R. Anti-SSEA-1 antibody or oligosaccharides containing a Galβ1→4 (Fucα1→3)GlcNAc terminus as inhibitors have been used to demonstrate that the SSEA-1 molecule may participate in adhesive events involved in compaction in early embryogenesis.

There are four different β1→6 N-acetylglucosaminyl linkages, as follows: (1) GlcNAcβ1→3(GlcNAcβ1→6)Gal, the IGnT product (Piller et al., *J. Biol. Chem.*, 259:13385–13390 (1984), which is incorporated herein by reference); (2) Galβ1→3(GlcNAcβ1→6)GalNAc, the core 2 structure (Piller et al., *J. Biol. Chem.*, 263:15146–15150 (1988), which is incorporated herein by reference); (3) GlcNAcβ1→3(GlcNAcβ1→6)GalNAc, the core 4 structure (Brockhausen et al. *Biochemistry*, 24:1866–1874 (1985), which is incorporated herein by reference) and (4) GlcNAcβ1→2(GlcNAcβ1→6) Man, the N-acetylglucosaminyltransferase V product (Cummings et al., *J.Biol. Chem.*, 257:13421–13427 (1982), which is incorporated herein by reference). The enzymes responsible for each of these linkages share the same unique property that Mn$^{2+}$ is not required for their activity. Thus far, the cDNAs encoding only IGnT and core 2β-1,6-N-acetylglucosaminyltransferase (C2GnT) have been cloned. Bierhuizen and Fukuda, *Proc. Natl. Acad. Sci., USA*, 89:9326–9330 (1992), which is incorporated herein by reference, have recently reported that Galβ1→3GalNAc is the only substrate for C2GnT.

Figure 2:
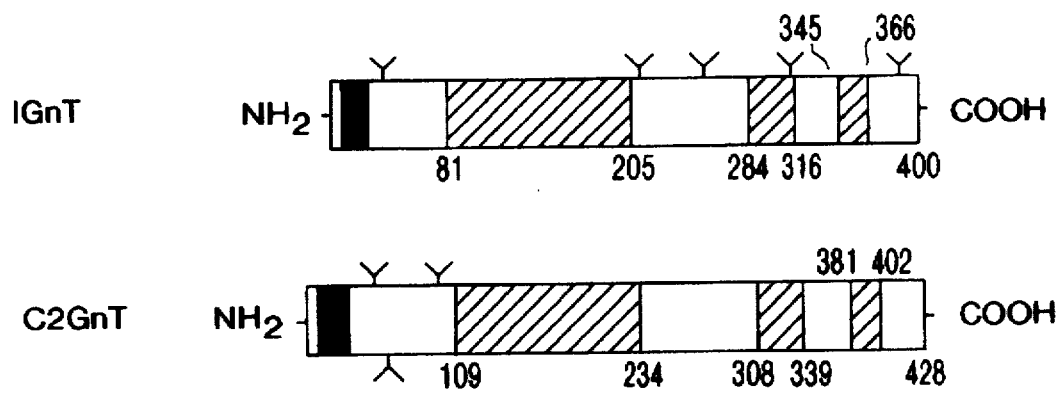
FIG. 2 depicts the domain structures and homologous regions of IGnT and C2GnT (core 2β1,6-N-acetylglucosaminyltransferase). Alignment of the two β-1, 6-N-acetylglucosaminyltransferases cloned to date reveals a 126 amino acid sequence having 60% sequence identity, a 33 (or 32) amino acid sequence having greater than 59% identity and a 22 amino acid sequence having 59% identity (hatched boxes). Closed boxes indicate the signal anchor domain and "Y" indicates potential N-glycosylation sites.

The cloned glycosyltransferases share a common type II transmembrane topology that consists of a short amino terminal cytoplasmic sequence, a signal-anchor sequence followed by a short stem region and a large carboxyl terminal catalytic domain. Apart from this common topology. IGnT and C2GnT have no apparent homology with other glycosyltransferases including two other N-acetylglucosaminyltransferases. Comparison of the amino acid sequences of IGnT and C2GnT reveals a limited but distinct homology. As shown in FIG. 2, a region of high homology is located in a sequence near the center of the presumed catalytic domain (see, also, FIG. 3). In addition, two regions near the COOH-terminus of the enzymes have modest degrees of homology (FIG. 2; see, also, FIGS. 4 and 5). As previously reported, the intraluminal domain contains the catalytic activity of the transferases (Colley et al., 1989, which is incorporated herein by reference; Kukowska-Latallo et al. 1990; Bierhuizen and Fukuda, 1992).

Wen et al., *J. Biol. Chem.*, 267:21011–21019 (1992), which is incorporated herein by reference, reported that there is homology in a region of the amino acid sequences of three different sialyltransferases; Galβ1→3(4) GlcNAcα-2,3-sialyltransferase,Galβ1→GalNAcα-2,3-sialyltransferase and Galβ1→4GlcNacα-2,6-sialyltransferase. This region of homology is in the center of the catalytic domains of these enzymes, in a similar location with respect to the domain structures of IGnT and C2GnT (FIG. 2). However, the extent of the homology between IGnT and C2GnT is much greater than the homology between the three sialyltransferases. Since this region of homology is not observed in other N-acetylglucosaminyltransferases, it is unlikely that this region represents the binding site for UDP-GlcNAc.

In the β-1,6-N-acetylglucosaminyltransferase gene family there are two additional regions close to the COOH terminus where modest but distinct homology is present (FIG. 2; see, also, FIGS. 4 and 5). Thus, it is possible the three regions of homology are close to each other in the folded three-dimensional protein structures. If this is the case, the conserved sequences may be essential to forming the correct framework necessary for allowing specific amino acids to bind to the acceptor. In this regard, the three-dimensional structure formed by the carbohydrate recognition domain of C-type lectins has been determined. These results suggest that the conserved amino acid residues in the carbohydrate recognition domain are involved in generating characteristic folding patterns, which are likely shared by different C-type lectins (Weis et al., *Nature*, 360:127–134 (1992), which is incorporated herein by reference) and are involved in calcium or carbohydrate binding.

The availability of a cDNA clone encoding the I branching enzyme, IGnT, enables one to regulate the amount of I branching by regulating the transcription level of the I branching enzyme. For example, one can express I branches in sialyl Le$^x$ expressing cells, then examine whether such branches increase binding to E-selectin. One can also reduce or abolish the expression of the I branching enzyme using antisense technology or gene knock-out in transgenic mice in order to identify the critical role for I branching during embryonic development and differentiation.

The expression of all of the β-1,6-N-acetylglucosaminyltransferases changes dramatically during development and oncogenesis. Thus, the occurrence of the I antigen is closely associated with development and maturation of erythroid cells (Marsh, *Br. J. Haematol.*, 7:200–209 (1961); Fukuda et al., *J. Biol. Chem.*, 254:3700–3703 (1979), each of which is incorporated herein by reference), whereas the formation of the core 2 structure in O-glycans occurs in a variety of biological processes such as T-cell activation (Piller et al., 1988) and immunodeficiency occurring in Wiskott-Aldrich syndrome (Piller et al., *J. Exp. Med.*, 173:1501–1510 (1991), which is incorporated herein by reference) and in AIDS (Saitoh et al., *Blood*, 77:1491–1499 (1991), which is incorporated herein by reference). Also, an increase in the activities of N-acetylglucosaminyltransferase V and C2GnT have been associated with malignant transformation (Yamashita et al., *J. Biol. Chem.*, 259:10634–10650 (1984); Pierce and Arango, *J. Biol. Chem.*, 261:10772–10777 (1986); Yousefi et al., *J. Biol. Chem.*, 266:1772–1782 (1991), each of which is incorporated herein by reference). The present invention suggests that these enzymes, the activity of which change dramatically during development and oncogenesis, have evolved from a common precursor gene. Thus, the expression of these enzymes likely is regulated by common gene regulatory elements as well as intrinsic genomic elements. An understanding of the genomic relationship of the different β-1,6-N-acetylglucosaminyltransferases and their regulation in expression during development and oncogenesis is extremely important in order to elucidate the role of carbohydrates in development and oncogenesis.

In addition to the expression of IGnT, the levels of polylactosaminoglycan synthesis are controlled by the expression of two other β-1,6-N-acetylglucosaminyltransferases, C2GnT, for O-glycans, and N-acetylglucosaminyltransferase V, for N-glycans. The expression of the latter two enzymes appears to, be differentially regulated during cell differentiation and in malignancy. Since these β-1,6-N-acetylglucosaminyltransferases are likely to regulate carbohydrate-protein interactions during development and in malignancy by regulating the amount of poly-N-acetyllactosamines and their terminal structures, it is essential to determine their gene structures and to define the mechanisms for the regulation of their expression.

Figure 6A:
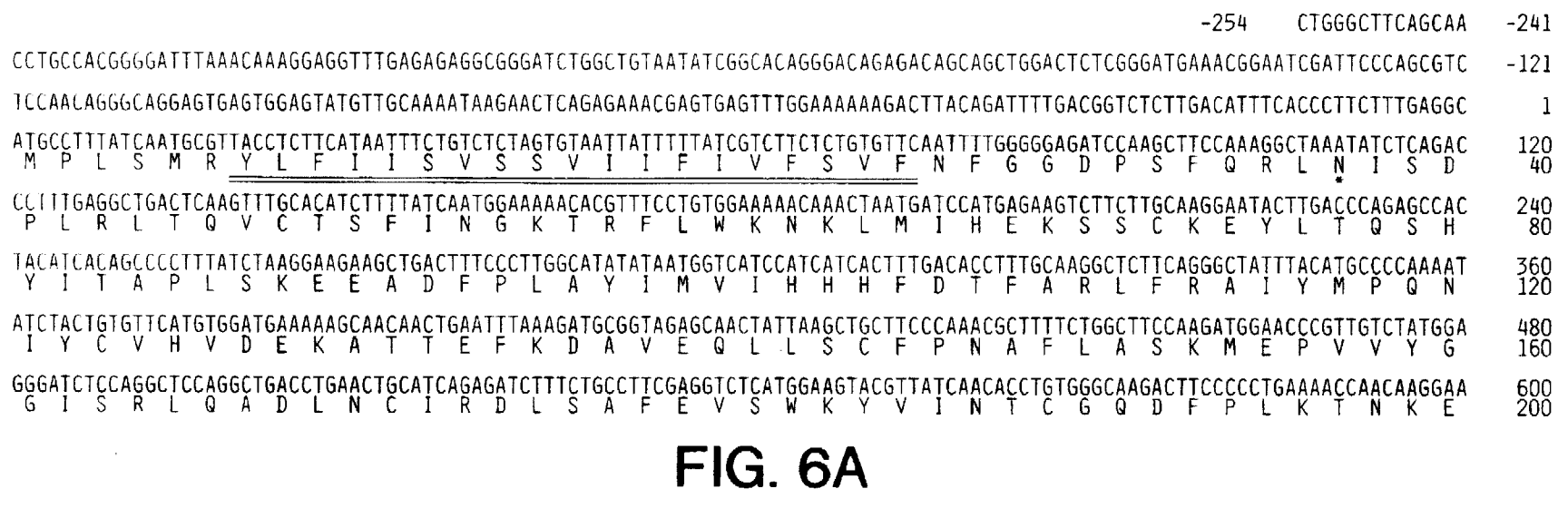
Figure 6B:
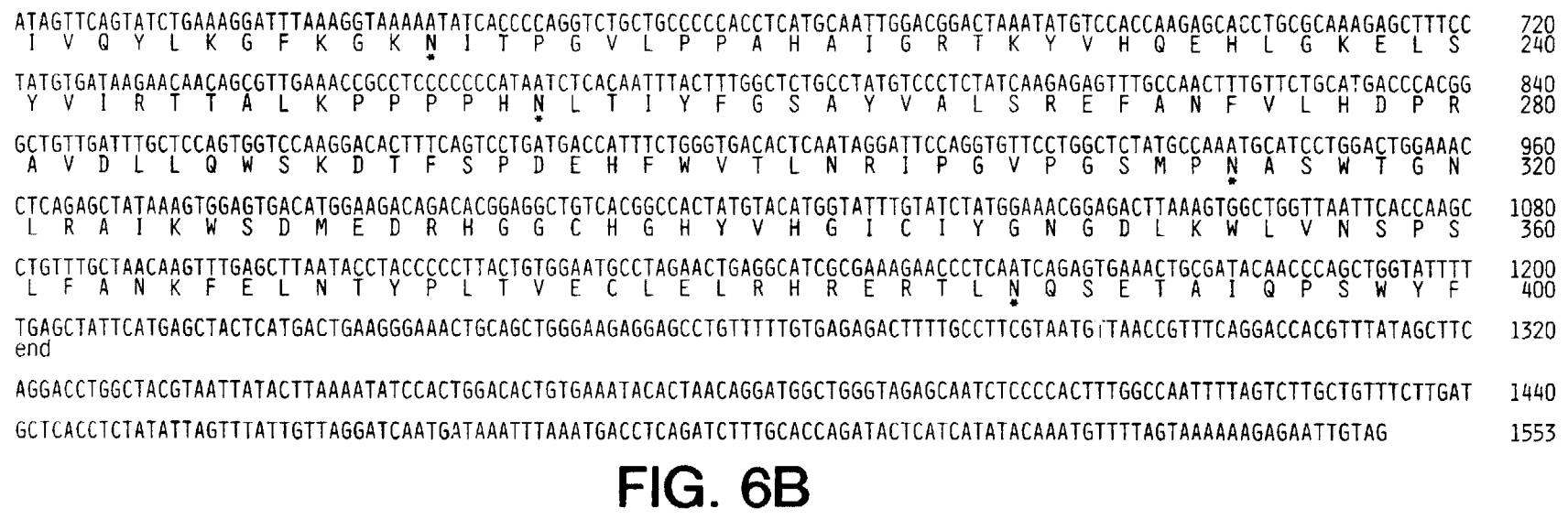

Accordingly, the present invention provides an isolated nucleic acid molecule encoding a human β-1,6-N-acetylglucosaminyltransferase, IGnT, (SEQ ID NO. 13)substantially the same as shown in FIG. 6. As used herein the term "human β-1, 6-N-acetylglucosaminyltransferase, the I-branching enzyme" ("IGnT"), refers to both the soluble and the membrane bound, biologically active fragments of the human IGnT expressed by the isolated nucleic acid.

The term "isolated nucleic acid molecule" as used herein means a nucleic acid molecule that is in a form that does not occur in nature. The nucleic acid sequence encoding soluble human IGnT is included within the nucleic acid sequence set forth in FIG. 6 (from about nucleotide position 94 to about 1200) or any portion thereof that binds to i antigen or the I antigen.

A human IGnT nucleic acid can be isolated, for example, by using a natural or artificially designed antibody to IGnT to probe a human cDNA expression library. Methods for screening such a library are well known in the art (see, for example, Gougos et al., *J. Biol. Chem.* 265:8361 (1990) which is incorporated herein by reference). DNA and cDNA molecules encoding human IGnT branching enzymes are useful for identifying and isolating complementary genomic DNA sequences, cDNA or RNA from humans or other mammalian or eukaryotic sources.

The invention also encompasses nucleic acid molecules that differ in sequence from the nucleic acid molecule shown in FIG. 6 but produce the same phenotypic effect. These phenotypically equivalent nucleic acid molecules are referred to herein as "equivalent nucleic acids." Equivalent nucleic acids, for example, can have different nucleotide sequences but, nevertheless, encode proteins having the same amino acid sequence, due to the degeneracy of the genetic code. The present invention further encompasses nucleic acid molecules characterized by having nucleotide changes in non-coding regions that do not alter the phenotype of the polypeptide produced therefrom when compared to the polypeptide produced from the nucleic acid molecule described in FIG. 6.

Also included within the scope of the invention are nucleic acid molecules that hybridize to the nucleic acid molecule of the subject invention. Such hybridizing nucleic acid molecules, referred to as "probes," can be prepared, for example, by nick translation of the nucleic acid molecule of FIG. 6, in which case the hybridizing nucleic acid molecules can be random fragments of the nucleic acid molecule disclosed in FIG. 6 (see, for example, Sambrook et al., *Molecular Cloning: A laboratory manual* (Cold Spring Harbor Laboratory Press, Cold Spring Harbor, N.Y., 1989), which is incorporated herein by reference). However, specific selected nucleic acid molecules of at least 10 nucleotides also are useful as probes and can be synthesized de novo, using methods well known in the art, or can be transcribed from various vectors specifically designed for that purpose and available from commercial sources. As used herein, the term "nucleic acid" encompasses RNA as well as single and double-stranded DNA and cDNA. In addition, the terms "enzyme," "glycosyltransferase" and "polypeptide" are used herein to generally include naturally occurring allelic variants of these substances as well as man-made recombinant forms.

The invention also provides the isolated nucleic acid molecules operatively linked to a promoter of RNA transcription, as well as other regulatory sequences. As used herein, the term "operatively linked" indicates the nucleic acid molecule is positioned in such a manner that the promoter will direct the transcription of RNA using the nucleic acid molecule as a template. Such promoters can direct transcriptional activity from a DNA-dependent RNA polymerase, which is known generally in the art as RNA polymerase, or from an RNA-dependent RNA polymerase, such as SP6, T4 and T7 RNA polymerase. One skilled in the art recognizes that a particular RNA polymerase requires a specific transcriptional start site, such as a TATA sequence or, for example, an SP6 promoter. Vectors containing an appropriate promoter as well as a cloning site into which a nucleic acid molecule is inserted and operatively linked to that promoter are well known in the art (see, for example, Sambrook et al. 1989). Such vectors, which are useful for transcribing RNA in vitro or in vivo, include, for example, the pGEM series (Promega Biotec, Madison, Wis.).

The invention also provides a vector comprising an isolated nucleic acid molecule encoding a human IGnT or an active fragment thereof. Examples of vectors are well known in the art and include vectors derived from a virus, such as a bacteriophage, a baculovirus or a retrovirus, and vectors derived from bacteria or a combination of bacterial and viral sequences, such as a cosmid or a plasmid (eg., pPSVEI-PyE and pZIPneo-leu).

A nucleic acid molecule is inserted into a vector using any of several methods well known in the art (see, for example, Sambrook et al. 1989). For example, a nucleic acid molecule to be inserted and a vector into which the molecule is to be inserted can be treated with a restriction enzyme, which creates complementary ends on the molecule and the vector, thus allowing the ends to base pair with each other and further allowing the nucleic acid molecules to be covalently linked using, for example, a DNA ligase. Alternatively, the nucleic acid molecule to be inserted can have ligated thereto synthetic nucleic acid linkers that correspond to a restriction site in the vector DNA. Following treatment of the DNA molecules with the appropriate restriction endonuclease, the sequences can be joined as described above.

A vector also can contain an oligonucleotide encoding, for example, a termination codon or other transcription or translation regulatory elements. The vector also can contain an appropriate restriction site, which can be used for inserting other useful nucleic acid molecules including, but not limited to a selectable marker gene, such as the neomycin gene, which is useful for selecting stable or transient transfectants in mammalian cells; enhancer sequences and promoter sequences, which are obtained, for example, from a viral, bacterial or mammalian gene; transcription termination and RNA processing signals, which are obtained from a gene or a virus such as SV40, such sequences providing, for example, stability of a transcribed mRNA sequence; an origin of replication obtained, for example, from SV40, polyoma or *E. coli*, which allow for proper episomal replication; versatile multiple cloning sites; and RNA promoters such as the above-described T7 and SP6 promoters, which allow for in vitro transcription of sense and antisense RNA.

Also provided are vectors comprising a DNA molecule encoding a human IGnT, the vectors being adapted for expression in a host cell such as a bacterial cell, a yeast cell, an insect cell, a mammalian cell and other animal cells. The vectors additionally comprise regulatory elements specifically required for expression of the DNA in a particular cell, the elements being located relative to the nucleic acid molecule encoding human IGnT so as to permit expression thereof. Regulatory elements required for expression have been described above and include transcription and translation start sites and termination sites. Such sites permit binding, for example, of RNA polymerase and ribosome subunits. A bacterial expression vector can include, for example, an RNA transcription promoter such as the lac promoter, a Shine-Delgarno sequence and an initiator AUG codon in the proper frame to allow translation of an amino acid sequence (Sambrook et al. 1989).

Similarly, an eucaryotic expression vector can include, for example, a heterologous or homologous RNA transcription promoter for RNA polymerase binding, a polyadenylation signal located downstream of the coding sequence, an AUG start codon in the appropriate frame and a termination codon to direct detachment of a ribosome following translation of the transcribed mRNA. Vectors having these and other characteristics are commercially available or are assembled by one skilled in the art using well known methods described, for example, by Sambrook et al. 1989. The expression vectors are useful for producing cells that express a glycosyltransferase such as IGnT.

The invention also provides a host cell, which contains a vector comprising a nucleic acid molecule encoding a human IGnT. An example of such a host cell is a mammalian cell comprising a plasmid adapted for expression in the mammalian cell. Such a plasmid comprises, for example, a cDNA molecule encoding a human IGnT and regulatory elements necessary for expression of the glycosyltransferase in the particular host cell. Various mammalian cells are useful as host cells including, for example, mouse NIH3T3 cells, CHO cells, HeLa cells and Ltk- cells. In addition, mammalian cells obtained, for example, from a primary explant culture are useful as host cells. Methods for introducing an expression plasmid such as a plasmid described above are well known in the art and include, for example, various methods of transfection such as the calcium phosphate, DEAE-dextran and lipofection methods, as well as electroporation and microinjection, all of which are described in detail in Sambrook et al. 1989.

The present invention further provides purified human IGnT (SEQ ID NO. 14) or a fragment thereof having the native enzymatic activity of human IGnT, which converts linear polylactosaminoglycan into branched poly-N-acetyllactosamines. Human IGnT can consist of a membrane bound form comprising a protein of approximately 400 amino acids in length and having a molecular mass of about 45,860 daltons and a type II transmembrane topology. The deduced amino acid sequence of the disclosed glycosyltransferase is set forth in FIG. 6. However, the membrane bound form of IGnT also can be an active fragment of IGnT which includes the transmembrane sequence and, therefore, is bound to a cell membrane.

In addition, the invention provides purified soluble human IGnT and an active fragment thereof. As used herein, "soluble human IGnT" means a biologically active fragment of the human IGnT expressed from all or a portion of the nucleic acid sequence encoding the extracellular domain of the glycosyltransferase shown in FIG. 6. The extracellular domain is encoded by a nucleic acid sequence comprising about nucleotides 94 to 1200 in the nucleic acid sequence of FIG. 6. A soluble human IGnT expressed from such a nucleic acid sequence is secreted from a cell expressing the IGnT activity and, therefore, is not present as the membrane-bound form of IGnT. The term "soluble human IGnT" further includes a non-naturally occurring cleaved polypeptide, which functions as a secreted molecule and retains the ability to bind to the ligands recognized by the membrane-bound form of IGnT, such ligands including, for example, the determinants that define the i/I antigens on a cell surface.

As used herein, human "IGnT" means a protein having an amino acid sequence that is substantially the same as the 400 amino acid sequence shown in FIG. 6 or a polypeptide or a peptide encoding an active fragment of IGnT. Use of the term "IGnT" is meant to include the soluble and the membrane-bound form of the human β-1,6-N-acetylglucosaminyltransferase, the I-branching enzyme, or a biologically active fragment of the enzyme, either of which is produced by expression of an isolated nucleic acid.

As used herein, an "active fragment," also referred to as a "biologically active fragment," means a portion of the IGnT amino acid sequence shown in FIG. 6 that has the native activity IGnT. As used herein, the "native" activity of IGnT means the enzymatic activity of IGnT, which binds i/I determinants and mediates the conversion of a linear polylactosaminoglycan (i antigen) into a branched poly-N-acetyllactosamine (I antigen). Methods for determining whether a fragment of IGnT can bind to and convert a linear polylactosaminoglycan into a branched poly-N-acetyllactosamine are disclosed herein and well known in the art. An active fragment of human IGnT includes a polypeptide encoded by a portion of the nucleic acid molecule shown in FIG. 6, which encodes a fragment of human IGnT, such as the soluble human IGnT described above, provided that the expressed fragment has the native activity of IGnT.

As used herein, the term "purified" means a molecule that is substantially free of contaminants normally associated with the molecule in a cell. For example, a purified membrane-bound form of IGnT is obtained using any of several methods, alone or in combination. Such methods are well known in the art and include precipitation, gel filtration, ion-exchange chromatography, reversed-phase high performance liquid chromatography and affinity chromatography. These and other methods are described in detail by Deutscher et al. (*Guide to Protein Purification: Methods in Enzymology* Vol. 182, (Academic Press 1990), which is incorporated herein by reference).

Alternatively, purified IGnT or an active fragment thereof can be obtained using recombinant DNA methods as described, for example, in Sambrook et al. 1989. For example, a nucleic acid encoding IGnT or an active fragment thereof is introduced into a suitable host cell, which can be induced to express the cloned nucleic acid sequence. Purified IGnT or the active fragment of IGnT is recovered from the cell using the methods disclosed above. A biologically active fragment of IGnT also can be produced by chemical synthesis using an Applied Biosystems, Inc. (Foster City, Calif.) Model 430A or 431automatic polypeptide synthesizer and chemicals provided by the manufacturer.

The invention also provides antisense oligonucleotides that can bind specifically with nucleic acid sequences encoding human IGnT. In many cases, antisense oligonucleotides are synthesized using nucleotide analogues, which confer desirable characteristics on the oligonucleotides such as endonuclease and exonuclease resistance.

Antisense oligonucleotides can be designed so as to specifically bind with a preselected sequence of the nucleic acid molecule shown in FIG. 6. Specific binding of an antisense oligonucleotide is useful, for example, for preventing transcription or translation of a mRNA encoding IGnT. As used herein, "specific binding" refers to the ability of a nucleic acid sequence to align with and hydrogen bond to a complementary nucleic acid sequence under relatively stringent hybridization conditions. Methods for approximating the stringency required for specific binding are well known in the art. In addition, the appropriate stringency can be empirically determined based on a calculated approximation (see, for example, Sambrook et al. 1989).

The invention also provides a pharmaceutical composition comprising a pharmaceutically acceptable carrier and an amount of an antisense oligonucleotide that effectively reduces expression of a human IGnT. As used herein, the term "pharmaceutically acceptable carrier" is meant to encompasses standard pharmaceutical carriers, such as water, phosphate buffered saline, emulsions such as an oil/water or water/oil emulsion and various types of wetting agents.

A pharmaceutical composition can include, for example, an oligonucleotide and a vehicle, which comprises a hydrophobic carrier molecule that facilitates introduction of the oligonucleotide through a cell membrane and specific binding with a nucleic acid encoding a human IGnT present in the cell. A liposome is an example of a hydrophobic carrier molecule. However, a pharmaceutically acceptable hydrophobic carrier also can be a structure that is recognized and bound by a particular cell surface receptor, which can be specific for a selected cell type into which one wishes to introduce the oligonucleotide. Such a structure can be part of a protein known to bind to a cell-type specific receptor such as the insulin molecule, which is useful for targeting β cells in the pancreas.

Antisense oligonucleotides are designed to specifically bind selected nucleic acid sequences. Specific binding can be to DNA sequences that encode IGnT mRNA, in which case transcription of the DNA sequences is inhibited, or to a sequence of the transcribed mRNA, in which case translation of the mRNA is inhibited. Thus, an antisense oligonucleotide is useful as a drug to inhibit expression of IGnT in a patient, where the patient's symptoms are related to overexpression of IGnT or to aberrant expression of i antigen or I antigen.

The invention provides a means to therapeutically alter levels of IGnT produced in a cell by using a synthetic antisense oligonucleotide drug ("SAOD"). The SAOD's or other antisense chemical structures designed to recognize and selectively bind to a preselected sequence of the nucleic acid molecule of FIG. 6, or a mRNA transcript of the molecule or chemically modified, synthetic nucleic acid based on the molecule, are constructed so as to be complementary to the preselected sequence.

The designed SAOD can be stable in the blood stream of a patient following injection or in the medium of a laboratory cell culture or can be degradable after a predetermined period of time. The designed SAOD also can readily traverse a cell membrane in order to enter the cytoplasm of the cell, if such traversal is desirable. An SAOD having the appropriate physical and chemical properties, which allow it to pass through a cell membrane is, for example, a small, hydrophobic SAOD or an SAOD that is recognized and transported into the cell by an active cell transport mechanism. Where desirable, the designed SAOD is recognized and transported only into a preselected cell population due to targeting the designed SAOD to a cell-type specific cellular uptake mechanism, as disclosed above.

The SAOD is designed so as to inactivate the target nucleic acid sequence by inducing, for example, endogenous enzymes that degrade the antisense oligonucleotide-target sequence complex, such as RNAse H which degrades DNA-RNA hybrids. Alternatively, a DNA-mRNA complex can result in inhibition of translation of the mRNA target by interfering with the binding of translation regulatory factors or ribosomes. In addition, an antisense oligonucleotide can be designed to have ribozyme activity or to contain a reactive chemical group which degrades or chemically modifies a target mRNA sequence. SAOD drugs are capable of such properties when directed against mRNA targets (see Cohen et al., TIPS, 10:435 (1989) and Weintraub, H., *Scient. Amer.*, page 40January (1990), each of which is incorporated herein by reference). An SAOD is as a particularly effective therapeutic agent if it can be administered in vivo and in vitro and can be used to reduce the level of IGnT in a patient having a clinical condition that may benefit from such reduced expression, such as an inflammatory response and metastatic carcinoma.

Also provided are antibodies having specific reactivity with IGnT or an active fragment thereof. Active fragments of antibodies, such as an Fab-2 or Fv fragment, are encompassed within the meaning of the term "antibody," as used herein. The antibodies of the invention can be produced by any method known in the art. For example, polyclonal and monoclonal antibodies can be produced using methods described, for example, by Harlow and Lane (*Antibodies: A Laboratory Manual* (Cold Spring Harbor Laboratory Press, Cold Spring Harbor, N.Y., 1988), which is incorporated herein by reference). IGnT or a fragment thereof can be used as an immunogen to generate such antibodies. In particular, a soluble IGnT or soluble fragment of IGnT is useful as an immunogen.

Modified antibodies such as chimeric antibodies, humanized antibodies and CDR-grafted or bifunctional antibodies can be produced by methods well known to those skilled in the art and, therefore, are considered to be within the contemplated invention. The antibodies can be used in the form of serum isolated from an immunized animal or the antibody can be purified from the serum or produced by a hybridoma cell line, by chemical synthesis or recombinant methods described, for example, in Harlow and Lane (1988) and in Sambrook et al. (1989). The antibodies are useful for identifying, for example, cells expressing IGnT or the presence of IGnT in a biological sample obtained from a subject or for purifying IGnT from a composition containing the glycosyltransferase.

Where the antibodies are used for detecting IGnT, detection can be in vitro as in a diagnostic assay of a sample obtained from a subject or in vivo for imaging the localization of IGnT in a subject. When administered in vivo, the antibodies can be administered as a pharmaceutical composition comprising the antibody and a pharmaceutically acceptable carrier. Immunological procedures useful for in vitro detection of a target IGnT protein or peptide in a sample include immunoassays that employ a detectable antibody. Such immunoassays include, for example, ELISA, Pandex microfluorimetric assay, agglutination assays, flow cytometry, serum diagnostic assays and immunohistochemical staining procedures. These and other methods are well known in the art and described, for example, by Harlow and Lane (1988). An antibody can be labelled so as to be detectable using various methods. For example, a detectable marker can be directly or indirectly attached to the antibody. Useful markers include, for example, radionuclides, enzymes, fluorogens, chromogens and chemiluminescent labels.

The invention also provides a transgenic nonhuman mammal expressing a nucleic acid molecule encoding human IGnT or an active fragment thereof. The nucleic acid molecule can encode normal human IGnT or can be mutated so that a variant human IGnT is expressed. Alternatively the nucleic acid molecule introduced into the transgenic non-human mammal can encode antisense IGnT DNA or mRNA, which hybridizes to the transgenic mammals' own DNA or mRNA encoding IGnT, thereby preventing expression of the mammals' IGnT. The invention further provides a transgenic nonhuman mammal comprising a nucleic acid molecule encoding a human IGnT and an inducible promoter which provides a means to produce variable levels of IGnT expression and, consequently, I antigen expression on a cell.

The invention further provides a method for modifying a biological function mediated by the regulatory activity of IGnT comprising contacting a suitable sample containing a linear polylactosaminoglycan with an effective amount of IGnT or a biologically active fragment thereof or a pharmaceutical composition containing IGnT or the fragment. As used herein, "an effective amount" means an amount of the IGnT protein or peptide sufficient to induce the conversion of the i determinant on the linear polylactosaminoglycan to the I branched form or to inhibit the conversion of the i determinant on the linear polylactosaminoglycan to the I branched form.

An effective amount of IGnT or a pharmaceutical composition comprising IGnT is an amount that is useful for modifying the biological function mediated by the regulatory activity of IGnT in a biological material in vitro, in vivo or ex vivo. As used herein, the term "biological material" means a cell, a tissue, an organ and an organism as well as an extract prepared from a cell, a tissue and an organ. If the method is practiced in vitro, contact with the biological material is effected by incubating the material with the IGnT. The ex vivo method is similar but includes the additional step of reintroducing the treated material into the subject.

The invention also provides a method of alleviating a pathologic condition caused by the conversion of a linear polylactosaminoglycan expressing i antigen into a branched structure that expresses I antigen comprising contacting a nucleic acid molecule encoding human IGnT or an active fragment thereof with an antisense oligonucleotide as disclosed above. Such contact prevents expression of human IGnT, which, in turn, prevents the conversion of a linear polylactosaminoglycan expressing i antigen into a branched structure that expresses I antigen. As used herein, a "pathologic condition" is a pathology arising as a result of human IGnT activity. Examples of such pathologic conditions include tumor cell adhesion to endothelium and leukocyte adhesion to inflammatory sites, which occur in association with the conversion of i antigen to I antigen.

The invention also provides a method of alleviating a pathologic condition caused by the underexpression of human IGnT comprising contacting the linear polylactosaminoglycan expressing i antigen with purified soluble human IGnT or an active fragment thereof. Upon contact, the linear polylactosaminoglycan, which expresses i antigen, binds with IGnT and is converted into a branched structure, which expresses I antigen. Thus, as well as the pathologies described above, the term "pathologic condition" also encompasses a pathology arising from the underexpression of IGnT. For example, the i antigen is expressed on erythrocytes of the fetus and neonate and is subsequently converted by IGnT into I antigen, which is crucial for organ development. Frequently, however, IGnT is underexpressed, resulting in fewer conversions of i antigen to the I branched form, a condition which increases the patient's susceptibility to Type II hypersensitivity reactions. Examples of such reactions include hemolytic disease of the newborn, autoimmune hemolytic anemias and thrombocytopenias.

The invention also provides a method of detecting the presence of linear polylactosaminoglycans expressing i antigen on the cell surface comprising contacting a sample of cells with IGnT or an active fragment thereof and detecting binding of IGnT or the fragment to the cell surface i antigenic determinant. The presence of such binding indicates the presence of the linear polylactosaminoglycan expressing i antigen.

It is understood that modifications which do not substantially affect the activity of the various nucleic acid and protein, polypeptide and peptide molecules of this invention are also included within the definition of these molecules. Accordingly, the following examples are intended to illustrate but not limit the present invention.

EXAMPLE I

Construction of stably transfected CHO cells expressing the polyoma virus large T antigen This example illustrates the construction of stably transfected CHO cells useful for identifying the transient expression of a nucleic acid molecule encoding IGnT.

A cloned CHO cell line, designated CHO-Py-leu, was used for transient expression cloning (Seed and Aruffo, Proc. Natl. Acad. Sci., USA, 84:3365–3369 (1987), which is incorporated herein by reference). Sasaki et al., J. Biol. Chem., 262:12059–12076 (1987), and Smith et al., J. Biol. Chem., 265:6225–6234 (1990), each of which is incorporated herein by reference) have reported that CHO cells express the linear i-antigen. The plasmid vectors, pPSVEI-PyE, which contains the polyoma virus early genes (Muller et al., Mol. Cell. Biol., 4:2406–2412 (1984), which is incorporated herein by reference), and pZIPneo-leu, which contains leukosialin (CD43) and neomycin cDNA, were constructed as described (Bierhuizen and Fukuda, 1992).

CHO cell lines expressing polyomavirus large T antigen and human leukosialin were established by cotransfecting CHODG44 cells with pPSVEI-PyE and pZIPneo-leu, followed by selection of cells expressing G418 resistance. Polyoma virus large T antigen-mediated replication of plasmids in these cell lines was assessed by measurement of the methylation status of the recombinant DNA (Heffernan and Dennis, Nucl. Acids. Res., 19:85–92 (1991), which is incorporated herein by reference) using pcDNAI harboring cDNA encoding galactosyltransferase (Aoki et al., Proc. Natl. Acad. Sci., USA, 89:4319–4323 (1992), which is incorporated herein by reference).

EXAMPLE II

Isolation of a human IGnT cDNA clone

This example demonstrates the use of CHO-Py-leu cells to identify and allow the isolation of a vector containing a nucleic acid insert coding for IGnT.

A cDNA library, pcDNAI-PA-I, was constructed essentially as described by Bierhuizen and Fukuda, 1992. Briefly, poly $(A)^{30}$ RNA was isolated from human PA-1 teratocarcinoma cells, which express a large amount of I branched structures in its polylactosaminoglycans (Fukuda et al., 1985), reverse transcribed and inserted into the mammalian expression vector pcDNAI (Invitrogen, San Diego, Calif.).

Plasmid DNA was transfected into CHO-Py-leu cells using lipofection. After a 64 hour expression period, cells were detached at 37° C. in PBS/5 mM EDTA, pH7.4, pooled, centrifuged and resuspended in cold PBS, containing 10 mM EDTA, 10% fetal calf serum, pH 7.4, and human anti-I antibodies (Step) as serum in 1:100 dilution. After 1 hour incubation on ice, the cells were washed and panned on dishes coated with goat anti-human IgM (Sigma, St. Louis, Mo.) as described by Wysocki and Sato, Proc. Natl. Acad. Sci., USA, 75:2844–2848 (1978), which is incorporated herein by reference).

Plasmid DNA was rescued from transfected CHO-Py-leu cells that adhered to the panning dishes and digested with DpnI to remove plasmids that were not replicated in transfected cells. Plasmids that remained intact were transformed into the host E. coli MC1061/P3 cells (Seed and Aruffo, 1987). Following this round of transformation, plasmid DNA was prepared and used for an additional round of screening by the same procedure. E. coli transformants isolated from this second enrichment were plated to yield four pools of approximately 2,000 colonies each.

Plasmid DNA was prepared from each plate and transfected separately into CHO-Py-leu cells, after which the transfected cells were screened by panning as described above. One of the plasmid pools yielded relatively more attached and partially agglutinated cells. Transformants corresponding to this group were plated again to yield eight pools of approximately 500 colonies each and replica plates were made. Plasmid DNA was prepared from the replica plates, transfected separately into CHO-Py-leu cells and transfectants were screened for the expression of the I antigen by immunofluorescence (see below). One of the plasmid pools was selected and, following three subsequent rounds of sib selection with sequentially smaller active pools, a single plasmid, pcDNAI-IGnT, that directed the expression of the I antigen at the cell surface was isolated.

EXAMPLE III

Immunofluorescence Microscopy of CHO Cells Expressing the I Branching Enzyme

This example provides the methodology used to identify transfected cells expressing a protein having the activity of IGnT.

Figure 7A:
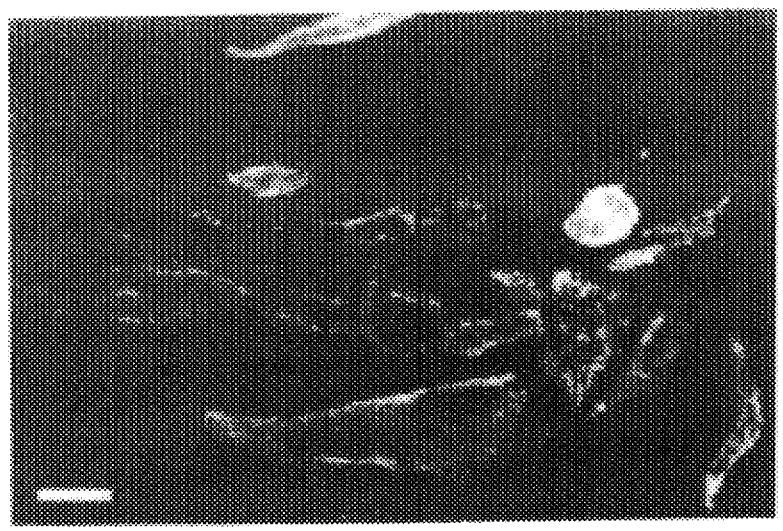
FIG. 7 shows expression of the I antigen in cells containing pcDNAI-IGnT. Cells were transfected with pcDNAI-IGnT (upper panel) or pcDNAI (lower panel) and examined by immunofluorescence staining using anti-I antigen antiserum (Ma). Cells were collected 64 hours after transfection, fixed and incubated with human anti-I serum (Ma) (1:100 dilution) followed by fluorescein isothiocyanate-conjugated goat anti-human IgM. Cells transfected with pcDNAI-IGnT expressed significant amounts of the I antigen (upper panel), whereas mock transfected cells did not express the I antigen (lower panel). Bar=20 μm.
Figure 7B:
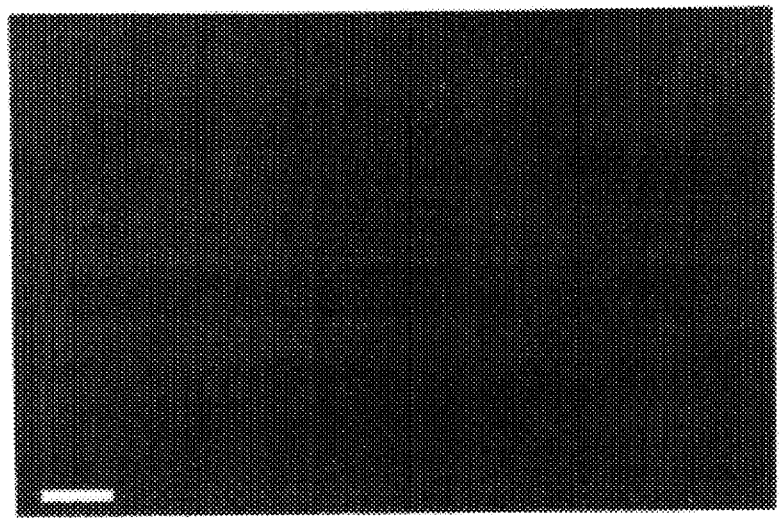

Sixty-four hours after transfection, transfected cells were fixed with 0.05% p-formaldehyde in PBS and stained with a 1:100 dilution of serum containing human anti-I antibody (Ma or Step), followed by fluorescein-conjugated goat anti-human IgM (Sigma, St. Louis, Mo.) in order to identify the transient expression of I antigen. The cells were examined under a Zeiss Axioplan microscope as described by Williams and Fukuda, *J. Cell Biol.*, 111:955–966 (1990), which is incorporated herein by reference. Representative results obtained using the anti-I antibody, Ma, are shown in FIG. 7. As shown, pcDNAI-IGnT transfected cells, but not pcDNAI transfected control cells, express significant amounts of the I antigen. The results indicate that the isolated pcDNAI-IGnT clone directs the conversion of i antigen to branched I antigen.

CHODG44 cells were transfected either with pSV2neo, alone, or with pSV2neo and pcDNAI-IGnT using a calcium phosphate method (Graham and Van der Eb, *Virology*, 52:456–467 (1973), which is incorporated herein by reference) and grown in the presence of G418 in order to select stable transfectants. Following G418 selection, clonal cell lines were isolated by limiting dilution to obtain CHO-neo and CHO-neo-IGnT cell lines, respectively. CHO-neo-IGnT cells were observed to express the I antigen recognized by human anti-I antibody (Ma), whereas CHO-neo cells showed no staining (not shown).

EXAMPLE IV

DNA Sequencing and Protein Analysis

This example provides the methodology for determining the sequence of the nucleic acid molecule encoding a protein having the activity of IGnT and for deducing the amino acid sequence of the protein, which was compared with previously reported protein sequences.

The cDNA insert present in pcDNAI-IGnT was sequenced using the dideoxy chain-termination method (Sanger et al., *Proc. Natl. Acad. Sci., USA*, 74:5463–5467 (1977), which is incorporated herein by reference). Oligonucleotide primers were synthesized according to the flanking sequences present in the plasmid. The nucleic acid sequence was extended by using oligonucleotide primers synthesized according to the nucleic acid sequence determined for the cDNA insert.

The 1807 base pair cDNA insert contains a single open reading frame (SEQ ID NO. 13) in the sense orientation with respect to the pcDNAI promoter (FIG. 6). The predicted reading frame encodes a 400 amino acid protein having a calculated molecular mass of 45,860 daltons (SEQ ID NO. 14). Based on hydropathy analysis, the protein was determined to have a type II transmembrane topology, which is characteristic of all mammalian glycosyltransferases cloned to date (see Paulson and Colley, 1989; Schachter, 1991; Joziasse, 1992). The type II transmembrane topology contains a very short cytoplasmic $NH_2$-terminal segment of six amino acid residues, followed by a 19-amino acid transmembrane domain that is flanked by basic amino acid residues. The COOH-terminal sequence, which presumably consists of the stem and catalytic domains is large and likely resides in the lumen of the Golgi complex. A consensus polyadenylation signal sequence was not found in the 3'-flanking sequence, suggesting that during construction of the library, cDNA synthesis was initiated at an A-rich sequence (nucleotides 1537–1547, see FIG. 6), rather than at the poly A tail.

Examination of the newly isolated sequence for homology with previously cataloged proteins revealed no significant similarity with any other sequences in the GeneBank database. Similarly, comparison of the sequence with glycosyltransferases cloned by others, including β-1,2-N-acetylglucosaminyltransferase I (Kumar et al., *Proc. Natl. Acad. Sci., USA*, 87:9948–9952 (1990), and Sarkar et al., *Proc. Natl. Acad. Sci., USA*, 88:234–238 (1991), each of which is incorporated herein by reference), and β-1,4-N-acetylglucosaminyltransferase III (Nishikawa et al., *J. Biol. Chem.*, 267:18199–18204 (1992), which is incorporated herein by reference), did not reveal any significant regions of homology.

When the newly isolated IGnT sequence was compared with C2GnT, limited but distinct homology was found in both the cDNA and the deduced amino acid sequences. In particular, when the amino acid sequences of the two glycosyltransferases were examined, a high degree of homology was present in what is presumed to be the catalytic domain (FIG. 3; see, also, FIG. 2). Furthermore, when the cDNA sequences of the glycosyltransferases were examined, two short regions showing modest homology were identified in-the COOH-terminal terminal half of the catalytic domain (FIGS. 4 and 5; see, also, FIG. 2). The homologous regions are shown schematically in FIG. 2. The results suggest that the two β-1,6-N-acetylglucosaminyltransferases are related evolutionarily.

EXAMPLE V

Northern blot analysis

This example demonstrates the expression of mRNA encoding IGnT in PA-1 cells and identifies the mRNA as a 4.4 kb transcript.

Poly $(A)^+$ RNA was prepared using a commercial RNA purification kit (Stratagene, La Jolla, Calif.), resolved by electrophoresis in a 1.2% agarose-2.2M formaldehyde gel and transferred onto a nylon membrane (Micro Separations Inc., MA) (Sambrook et al., 1989). The nucleic acid sequence encoding the putative catalytic domain of IGnT was amplified using PCR (Saiki et al. 1988), labeled with $[^{32}P]dCTP$ by a random priming method (Feinberg and Vogelstein, 1983) and used as a probe. Hybridizations were performed at 42° C. for 24 hours in buffers containing 50% formamide. Following hybridization, blots were washed several times in 0.1×SSPE/0.1% SDS at 42° C. for several hours (Sambrook et al., 1989) and exposed to Kodak XAR film at −70° C.

The cloned cDNA sequence hybridized to a single prominent 4.4 kb transcript in poly$(A)^+$ RNA from PA-1 cells (FIG. 8, lane 3) but was not detected in poly$(A)^+$ RNA isolated from CHO-Py-leu or HL-60 cells under the high stringency washing conditions (FIG. 8, lanes 1 and 2). This result is consistent with the reported presence of the I antigen in PA-1 cells (Fukuda et al., 1985) and its absence in CHO (Sasaki et al., 1987; Smith et al., 1990) and HL-60 cells (Mizoguchi et al., *J. Biol. Chem.*, 259:11949–11957 (1984), and Lee et al., *J. Biol. Chem.*, 265: 20476–20487 (1990), each of which is incorporated herein by reference).

EXAMPLE VI

Southern blot analysis

This example provides an analysis of the genomic DNA sequences encoding IGnT and C2GnT and suggests the existence of one or more other members of a family of glycosyltransferases, which includes IGnT and C2GnT.

Genomic DNA was analyzed by Southern blot hybridization using IGnT- and C2GnT-specific nucleic acid sequences as probes. Genomic DNA was prepared from HL-60 cells as described (Sambrook et al. 1989) and subjected to Southern blotting and hybridization as described previously (Siebert and Fukuda, *J. Biol. Chem.*, 261: 12433–12436 (1986), which is incorporated herein by reference).

Briefly, the blots were hybridized with cDNA probes in 6×SSPE, 0.5% SDS, 50 µg/ml denatured, sheared salmon sperm DNA containing 50% formamide at 42° C. for several hours, then washed in 2×SSPE/0.5% SDS at room temperature for several hours. The IGnT probe was prepared as described for northern blot analysis. The putative catalytic domain of C2GnT also was amplified by PCR as described by Bierhuizen and Fukuda, 1992, and labeled using a random priming method.

Figure 9:
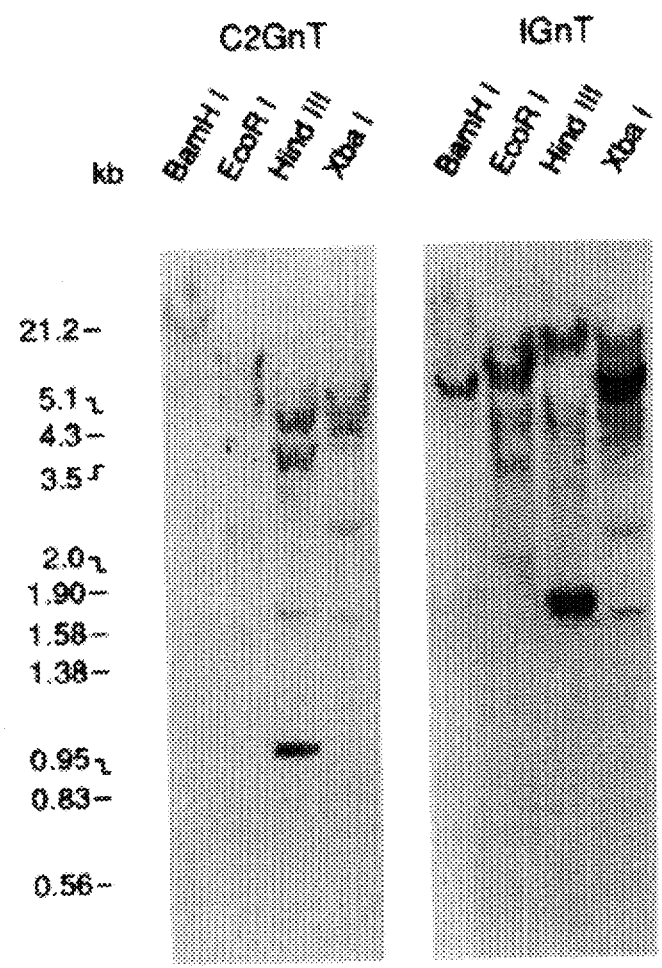
FIG. 9 shows a Southern blot analysis of human genomic DNA using IGnT- and C2GnT-specific probes. Following digestion of HL-60 cell genomic DNA with either BamHI, EcoRI, HindIII or XbaI (lanes 1–4, respectively), aliquots were separated in duplicate by agarose gel electrophoresis and transferred to nylon membranes. Blots were probed with a region of the cDNA of IGnT or C2GnT that encompasses only the putative intraluminal domain of the transferases. Mobility of molecular size markers are indicated at left (kilobases). Among the restriction enzymes employed, there is no restriction site in the coding sequence for BamHI, EcoRI and XbaI.

Following exposure of the blots to Kodak XAR-5 film at −70° C., several bands were observed to correlate to coding sequences. For example, 1.1 kb and 1.6 kb HindIII fragments represent the coding sequence for C2GnT and the IGnT, respectively (FIG. 9). In addition, the two sequences cross-hybridized with the cDNA probes under the low stringency conditions (data not shown). Several genomic fragments hybridized with one cDNA probe but not the other. In particular, a HindIII fragment of approximately 16 kb and a XbaI fragment of approximately 12 kb were detected by the IGnT probe but not the C2GnT probe. XbaI digestion yielded at least four fragments that were detected by both probes, even though there is no XbaI restriction site in either of the cDNA sequences. These results suggest that at least one more gene related to IGnT and C2GnT is present.

EXAMPLE VII

Amplification of genomic DNA sequences by polymerase chain reaction

This example provides a method for examining the structure of the IGnT and C2GnT genes in HL-60 cell genomic DNA.

In order to further understand the relationship between IGnT and C2GnT, the genomic sequences coding for the two enzymes were examined. The sequences were amplified by PCR using genomic DNA as HL-60 cell genomic DNA as template.

The 5' and 3' primers were synthesized according to the 5' and 3' flanking sequences of the IGnT and C2GnT cDNA sequences. The 5' and 3' primers for amplification of the IGnT gene start at position −154 with respect to the translation initiation site and at a position 232 nucleotides after the stop codon, respectively. The 5' and 3' primers for amplification of the C2GnT gene start at position −125 with respect to the translation initiation site and at a position 141 nucleotides after the stop codon, respectively.

Figure 10:
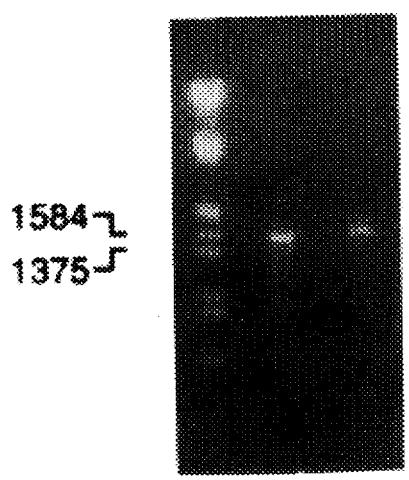
FIG. 10 shows the migration in a 1% agarose gel of PCR amplification products obtained from genomic DNA template sequences. The nucleotide sequences of IGnT and C2GnT were amplified by PCR and separated by agarose gel electrophoresis. The numbers at the left denote the size (in base pairs) of two molecular weight markers similar in size to the PCR products. Lanes 1 and 2, C2GnT; Lanes 3 and 4, IGnT. Lanes 1 and 3 were control lanes from PCR reactions that did not contain template genomic DNA.

Amplification of genomic DNA was repeated 35 times as follows: denaturation for 1 min at 94° C., annealing for 2 min at 55° C. and polymerization for 5 min at 68° C. Following amplification, the PCR products were subjected to 1.0% agarose gel electrophoresis. As shown in FIG. 10, the amplification products have the size expected for cDNA sequences of 1589 bp (IGnT) and 1553 bp (C2GnT). These results suggest that the complete coding sequences for IGnT and C2GnT are each contained within a single exon.

EXAMPLE VIII

Analysis of glycopeptides from CHO-neo and CHO-neo-IGnT cells

This example demonstrates that cells expressing the cloned IGnT nucleic acid molecule acquire the ability to convert i antigen to I antigen.

In order to confirm that the isolated cDNA sequence encodes IGnT, CHO cells were stably transfected with pcDNAI-IGnT and pSV2neo or with pSV2neo, alone. Following G418 selection, clonal cell lines were isolated by limiting dilution to obtain CHO-neo-IGnT and CHO-neo cell lines, respectively.

CHO-neo-IGnT cells and the control CHO-neo cells were metabolically labeled for 24 hours with [$^3$H]-galactose (10 µCi/ml) in A-MEM supplemented with 10% fetal calf serum. Labeled cells were harvested using a rubber policeman, washed with PBS and collected by centrifugation. The cell pellets were extracted with ten volumes of chloroform-methanol (2:1, v/v) as described by Fukuda et al. (1985) and the cell residues were digested with pronase for 24 hours at 60° C. in a toluene atmosphere.

Following pronase digestion, the samples were boiled for 10 minutes to denature any remaining enzyme. The samples were centrifuged to remove particulate matter and the supernatants were applied to a Sephadex G-50 Superfine column (1.0×110 cm) equilibrated with 0.1M NH$_4$HCO$_3$. Fractions containing high molecular weight glycopeptides were pooled, desalted and an aliquot was subjected to endo-β-galactosidase treatment as described by Fukuda and Matsumura, *J. Biol. Chem.*, 251:6218–6225 (1976), which is incorporated herein by reference. Digested glycopeptides and control glycopeptides both were fractionated by Sephadex G-50 gel filtration.

Figure 11A:
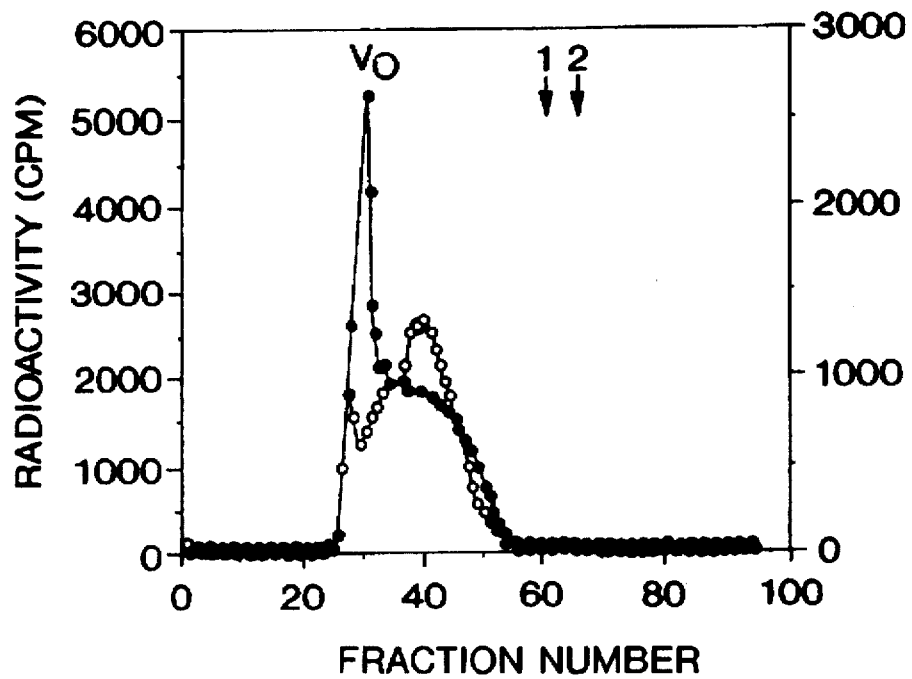
FIG. 11 shows the results of Sephadex G-50 gel filtration of $^3$H-galactose-labeled polylactosaminoglycans from CHO-neo (—○—) and CHO-neo-IGnT (—●—) cells. High molecular weight glycopeptides were prepared by pronase digestion of $^3$H-galactose-labeled cells and applied to Sephadex G-50 columns either before (left panel) or after endo-β-galactosidase treatment (right panel). The elution positions of standard structures are indicated: 1=NeuNAcα2→3Galβ1→4GlcNAcβ1→3Gal; 2=GlcNAcβ1→3Gal.
Figure 11B:
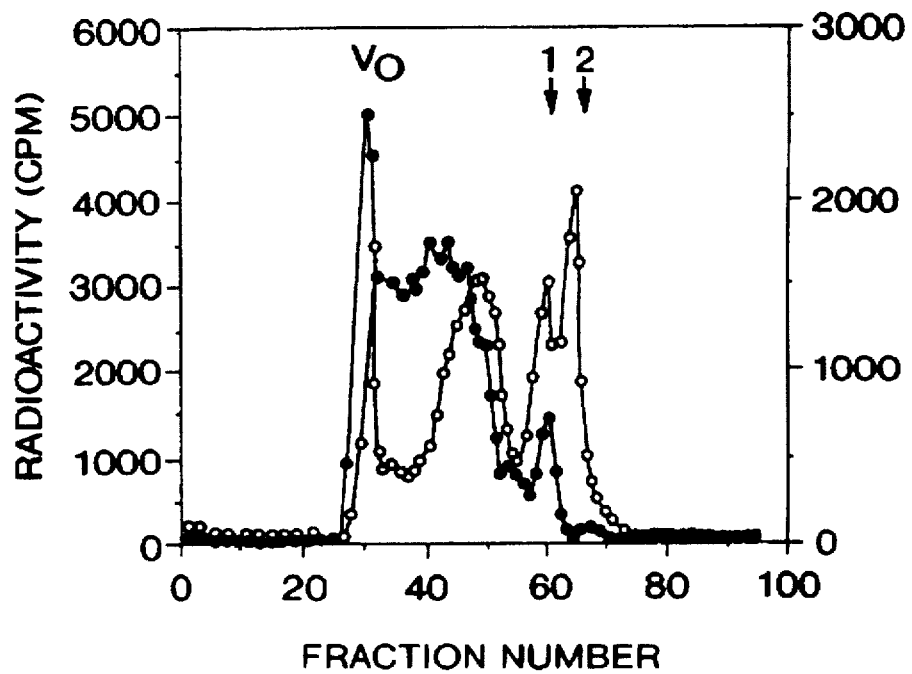

FIG. 11 demonstrates that CHO-neo-IGnT cells produced more glycopeptides having higher molecular weights than were produced by the CHO-neo cells. When the glycopeptides were digested with endo-β-galactosidase glycopeptides from CHO-neo-IGnT cells were more resistant to the enzyme treatment and yielded much less disaccharide, GlcNAcβ1→3Gal (FIG. 11), which can be produced only from a linear polylactosaminoglycan chain that contains at least three N-acetyllactosamine repeats (see Fukuda et al., *J. Biol. Chem.*, 253:6814–6819 (1978), which is incorporated herein by reference, and Fukuda et al., 1979). On the other hand, the branched galactose present in the I-antigen is resistant to endo-β-galactosidase treatment (Fukuda et al., 1978). These results indicate that the I antigenic structure is formed in CHO-neo-IGnT cells.

EXAMPLE IX

Methylation Analysis

This example demonstrates that cells expressing the cloned IGnT nucleic acid molecule produce a glycosyl linkage catalyzed by native IGnT.

The glycopeptides obtained from the [$^3$H]-galactose labeled CHO-neo and CHO-neo-IGnT cells were purified as described in Example IX and methylated as described by Ciucanus and Kerek, *Carbohydr. Res.*, 131:209–217 (1984), which is incorporated herein by reference. Prior to methylation, non-radioactive glycopeptides prepared from fetuin (Sigma, St. Louis, Mo) were added as a carrier. The methylated glycopeptides were dissolved in chloroform, washed five times with water and dried under a nitrogen stream, then hydrolyzed in 3N HCl for 3 hr at 80° C. After drying the hydrolysates under a nitrogen stream, the partially methylated galactose residues were dissolved in a small volume of chloroform-methanol (1:1, v/v), applied to a silica gel G plate and subjected to thin layer chromatography in acetone:water:ammonium hydroxide (250:3:1.5, v/v/v) as described by Lee et al., 1990. Following chromatography, the sample lanes were separated into 0.5 cm sections and radioactivity was determined by liquid scintillation counting.

Figure 12A:
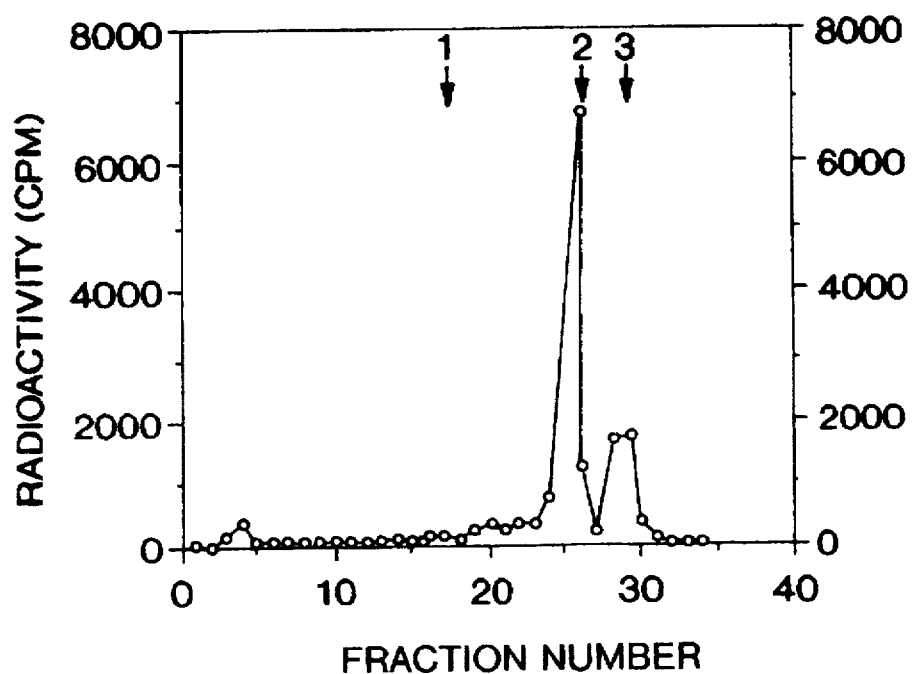
FIG. 12 shows the methylation analysis of $^3$H-galactose labeled glycopeptides. The glycopeptides as shown in the left panel of FIG. 11 were subjected to methylation analysis. The partially O-methylated galactose residues were separated by thin layer chromatography. The elution positions of standard methylated galactose residues are indicated: 1=2,4-di-O-methylgalactose; 2=2,4,6-tri-O-methylgalactose; and 3=2,3,4,6-tetra-O-methylgalactose. The occurrence of 2,4-di-O-methylgalactose residues (#1) in CHO-neo-IGnT cells (right panel), as opposed to CHO-neo cells (left panel), clearly indicates the presence of galactose substituted at both the 3- and 6- positions in these cells.
Figure 12B:
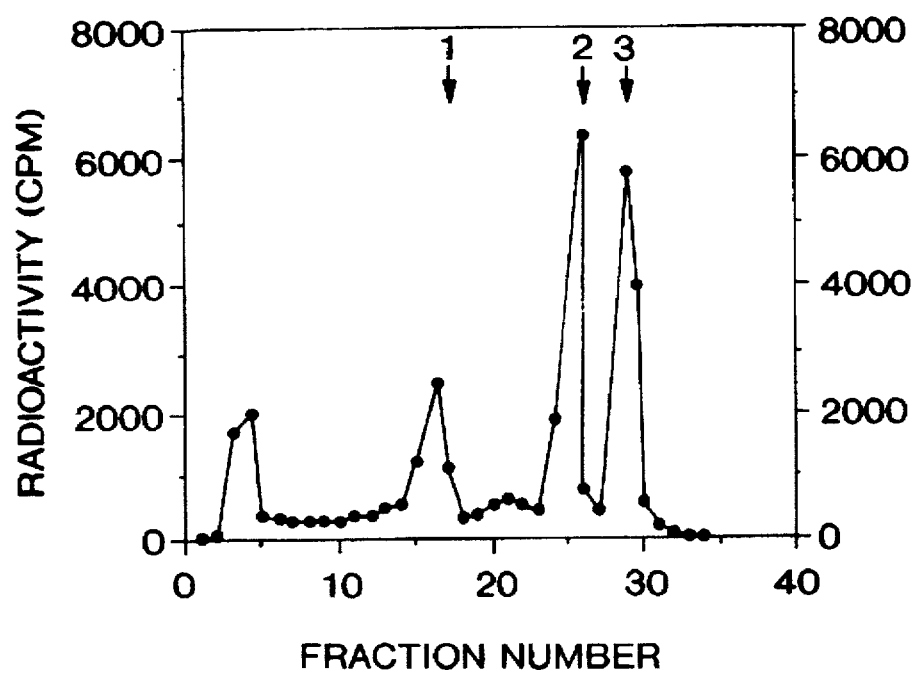

Methylation analysis of the $^3$H-galactose labeled glycopeptides demonstrated the presence of galactose substituted at positions 3 and 6 (2,4-di-O-methylgalactose) in CHO-neo-IGnT cells. These substitutions were not present in glycopeptides obtained from the control CHO-neo cells (FIG. 12). These results demonstrate that the CHO-neo-IGnT cells acquired the ability to form a GlcNAcβ1→6 linkage as a result of the expression of IGnT.

EXAMPLE X

In situ chromosome hybridization

This example demonstrates that IGnT is located on human chromosome 9 at the same locus which contains C2GnT.

In order to further understand how these two proteins are related, chromosomal localization of the genes encoding the glycosyltransferases was determined by in situ chromosome hybridization. In situ hybridization was performed on chromosome preparations obtained from human lymphocytes cultured in the presence of phytohemagglutinin for 72 hours. The conditions for labeling the probes, hybridization and washing were as described by Nguyen et al., *J. Cell. Biol.*, 102:711–715 (1986), which is incorporated herein by reference.

Figure 13:
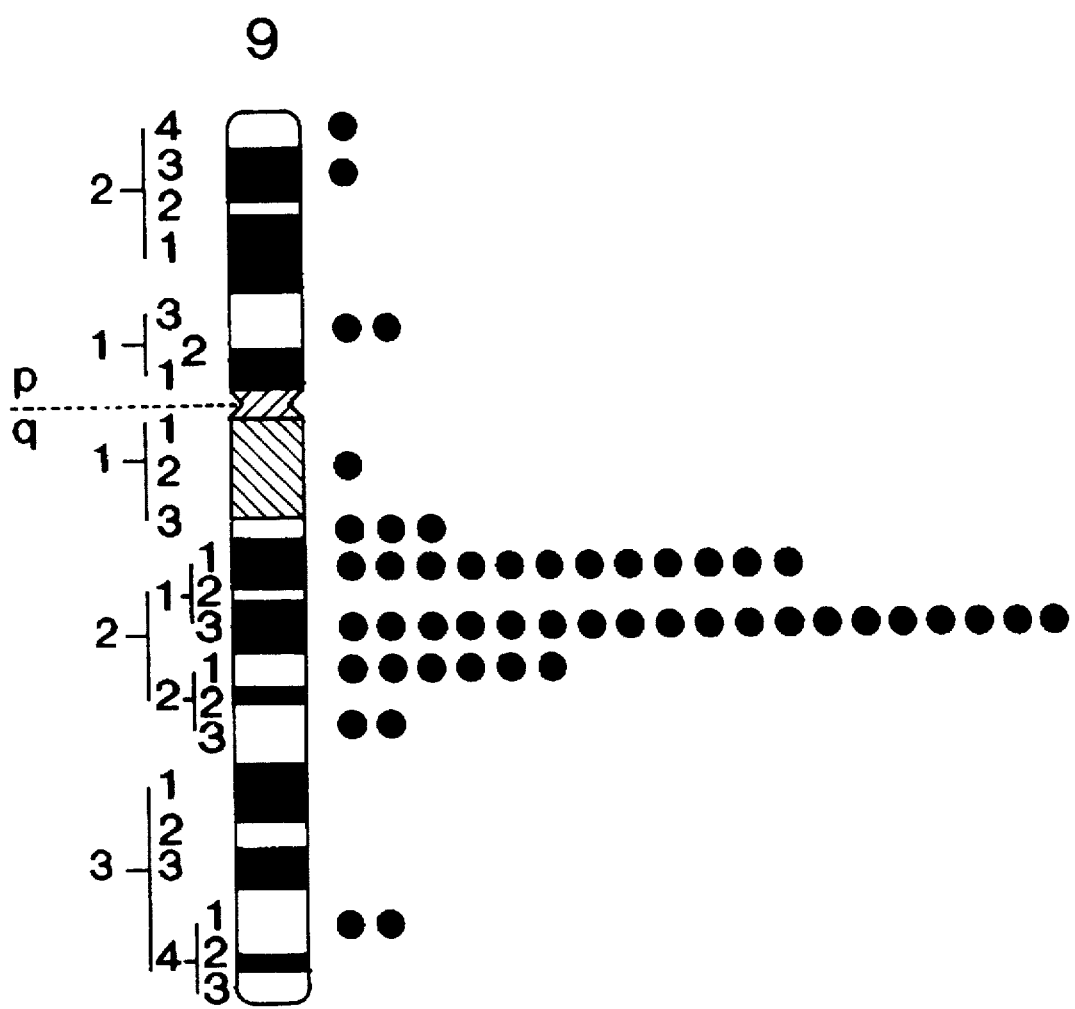
FIG. 13 shows the distribution of labeled sites on chromosome 9 for C2GnT. Of 100 metaphase cells examined for this hybridization, 241 silver grains were associated with chromosomes, 49 of which were located on chromosome 9 (20.3%). Seventy-six percent of the grains located on chromosome 9 mapped to the q21.1–22.1 region, with the greatest number appearing at the q21 band. Nearly identical results were obtained for IGnT, except that an additional minor peak occurred at p23 of chromosome 6.

Slides were coated with nuclear truck emulsion (Kodak NTB$_2$), then exposed for 19 days at 4° C. and developed. To avoid any slipping of silver grains during the banding procedure, chromosome spreads were first stained with a buffered Giemsa solution and metaphase chromosomes were photographed. R-banding was then performed using the fluorescence-photolysis-Giemsa method and the metaphase chromosomes were photographed before analysis. In general, 100–200 metaphase cells were examined for minimizing the statistical error caused by background staining. As shown in FIG. 13, the gene encoding C2GnT was localized to the q21 band of chromosome 9. Surprisingly, the gene encoding IGnT localized to the same locus.

Although the invention has been described with reference to the disclosed embodiments, it should be understood that various modifications can be made without departing from the spirit of the invention. Accordingly, the invention is limited only by the following claims.

---

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 378 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..378

( x i ) SEQUENCE DESCRIPTION: SEQ ID NO:1:

```
TAC ATC ACA GCC CCT TTA TCT AAG GAA GAA GCT GAC TTT CCC TTG GCA       48
Tyr Ile Thr Ala Pro Leu Ser Lys Glu Glu Ala Asp Phe Pro Leu Ala
 1               5                  10                  15

TAT ATA ATG GTC ATC CAT CAT CAC TTT GAC ACC TTT GCA AGG CTC TTC       96
Tyr Ile Met Val Ile His His His Phe Asp Thr Phe Ala Arg Leu Phe
                 20                  25                  30

AGG GCT ATT TAC ATG CCC CAA AAT ATC TAC TGT GTT CAT GTG GAT GAA      144
Arg Ala Ile Tyr Met Pro Gln Asn Ile Tyr Cys Val His Val Asp Glu
             35                  40                  45

AAA GCA ACA ACT GAA TTT AAA GAT GCG GTA GAG CAA CTA TTA AGC TGC      192
Lys Ala Thr Thr Glu Phe Lys Asp Ala Val Glu Gln Leu Leu Ser Cys
         50                  55                  60

TTC CCA AAC GCT TTT CTG GCT TCC AAG ATG GAA CCC GTT GTC TAT GGA      240
Phe Pro Asn Ala Phe Leu Ala Ser Lys Met Glu Pro Val Val Tyr Gly
 65                  70                  75                  80

GGG ATC TCC AGG CTC CAG GCT GAC CTG AAC TGC ATC AGA GAT CTT TCT      288
Gly Ile Ser Arg Leu Gln Ala Asp Leu Asn Cys Ile Arg Asp Leu Ser
                 85                  90                  95

GCC TTC GAG GTC TCA TGG AAG TAC GTT ATC AAC ACC TGT GGG CAA GAC      336
Ala Phe Glu Val Ser Trp Lys Tyr Val Ile Asn Thr Cys Gly Gln Asp
                100                 105                 110
```

```
TTC  CCC  CTG  AAA  ACC  AAC  AAG  GAA  ATA  GTT  CAG  TAT  CTG  AAA                          378
Phe  Pro  Leu  Lys  Thr  Asn  Lys  Glu  Ile  Val  Gln  Tyr  Leu  Lys
          115                 120                      125
```

( 2 ) INFORMATION FOR SEQ ID NO:2:

( i ) SEQUENCE CHARACTERISTICS:
        ( A ) LENGTH: 126 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Tyr  Ile  Thr  Ala  Pro  Leu  Ser  Lys  Glu  Glu  Ala  Asp  Phe  Pro  Leu  Ala
 1                     5                    10                         15

Tyr  Ile  Met  Val  Ile  His  His  His  Phe  Asp  Thr  Phe  Ala  Arg  Leu  Phe
               20                   25                         30

Arg  Ala  Ile  Tyr  Met  Pro  Gln  Asn  Ile  Tyr  Cys  Val  His  Val  Asp  Glu
          35                   40                        45

Lys  Ala  Thr  Thr  Glu  Phe  Lys  Asp  Ala  Val  Glu  Gln  Leu  Leu  Ser  Cys
     50                   55                        60

Phe  Pro  Asn  Ala  Phe  Leu  Ala  Ser  Lys  Met  Glu  Pro  Val  Val  Tyr  Gly
 65                     70                   75                         80

Gly  Ile  Ser  Arg  Leu  Gln  Ala  Asp  Leu  Asn  Cys  Ile  Arg  Asp  Leu  Ser
               85                   90                        95

Ala  Phe  Glu  Val  Ser  Trp  Lys  Tyr  Val  Ile  Asn  Thr  Cys  Gly  Gln  Asp
               100                  105                       110

Phe  Pro  Leu  Lys  Thr  Asn  Lys  Glu  Ile  Val  Gln  Tyr  Leu  Lys
          115                  120                       125
```

( 2 ) INFORMATION FOR SEQ ID NO:3:

( i ) SEQUENCE CHARACTERISTICS:
        ( A ) LENGTH: 378 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..378

( x i ) SEQUENCE DESCRIPTION: SEQ ID NO:3:

```
TAT  ATT  GTA  GAA  CCC  CTT  AGT  AAA  GAA  GAG  GCG  GAG  TTT  CCA  ATA  GCA    48
Tyr  Ile  Val  Glu  Pro  Leu  Ser  Lys  Glu  Glu  Ala  Glu  Phe  Pro  Ile  Ala
 1                     5                    10                         15

TAT  TCT  ATA  GTG  GTT  CAT  CAC  AAG  ATT  GAA  ATG  CTT  GAC  AGG  CTG  CTG    96
Tyr  Ser  Ile  Val  Val  His  His  Lys  Ile  Glu  Met  Leu  Asp  Arg  Leu  Leu
               20                   25                         30

AGG  GCC  ATC  TAT  ATG  CCT  CAG  AAT  TTC  TAT  TGC  GTT  CAT  GTG  GAC  ACA   144
Arg  Ala  Ile  Tyr  Met  Pro  Gln  Asn  Phe  Tyr  Cys  Val  His  Val  Asp  Thr
          35                   40                        45

AAA  TCC  GAG  GAT  TCC  TAT  TTA  GCT  GCA  GTG  ATG  GGC  ATC  GCT  TCC  TGT   192
Lys  Ser  Glu  Asp  Ser  Tyr  Leu  Ala  Ala  Val  Met  Gly  Ile  Ala  Ser  Cys
     50                   55                        60

TTT  AGT  AAT  GTC  TTT  GTG  GCC  AGC  CGA  TTG  GAG  AGT  GTG  GTT  TAT  GCA   240
Phe  Ser  Asn  Val  Phe  Val  Ala  Ser  Arg  Leu  Glu  Ser  Val  Val  Tyr  Ala
 65                     70                   75                         80

TCG  TGG  AGC  CGG  GTT  CAG  GCT  GAC  CTC  AAC  TGC  ATG  AAG  GAT  CTC  TAT   288
Ser  Trp  Ser  Arg  Val  Gln  Ala  Asp  Leu  Asn  Cys  Met  Lys  Asp  Leu  Tyr
```

|  |  |  |  |  |  |  |  |  |  |  |  |  |  |  |
|---|---|---|---|---|---|---|---|---|---|---|---|---|---|---|
|  |  |  |  | 85 |  |  |  | 90 |  |  |  | 95 |  |  |

```
GCA ATG AGT GCA AAC TGG AAG TAC TTG ATA AAT CTT TGT GGT ATG GAT    336
Ala Met Ser Ala Asn Trp Lys Tyr Leu Ile Asn Leu Cys Gly Met Asp
            100                 105                 110

TTT CCC ATT AAA ACC AAC CTA GAA ATT GTC AGG AAG CTC AAG            378
Phe Pro Ile Lys Thr Asn Leu Glu Ile Val Arg Lys Leu Lys
        115                 120                 125
```

( 2 ) INFORMATION FOR SEQ ID NO:4:

( i ) SEQUENCE CHARACTERISTICS:
        ( A ) LENGTH: 126 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Tyr Ile Val Glu Pro Leu Ser Lys Glu Glu Ala Glu Phe Pro Ile Ala
 1               5                  10                  15

Tyr Ser Ile Val Val His His Lys Ile Glu Met Leu Asp Arg Leu Leu
            20                  25                  30

Arg Ala Ile Tyr Met Pro Gln Asn Phe Tyr Cys Val His Val Asp Thr
            35                  40                  45

Lys Ser Glu Asp Ser Tyr Leu Ala Ala Val Met Gly Ile Ala Ser Cys
 50                  55                  60

Phe Ser Asn Val Phe Val Ala Ser Arg Leu Glu Ser Val Val Tyr Ala
 65                  70                  75                  80

Ser Trp Ser Arg Val Gln Ala Asp Leu Asn Cys Met Lys Asp Leu Tyr
            85                  90                  95

Ala Met Ser Ala Asn Trp Lys Tyr Leu Ile Asn Leu Cys Gly Met Asp
            100                 105                 110

Phe Pro Ile Lys Thr Asn Leu Glu Ile Val Arg Lys Leu Lys
        115                 120                 125
```

( 2 ) INFORMATION FOR SEQ ID NO:5:

( i ) SEQUENCE CHARACTERISTICS:
        ( A ) LENGTH: 99 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..99

( x i ) SEQUENCE DESCRIPTION: SEQ ID NO:5:

```
TTG CTC CAG TGG TCC AAG GAC ACT TTC AGT CCT GAT GAG CAT TTC TGG    48
Leu Leu Gln Trp Ser Lys Asp Thr Phe Ser Pro Asp Glu His Phe Trp
 1               5                  10                  15

GTG ACA CTC AAT AGG ATT CCA GGT GTT CCT GGC TCT ATG CCA AAT GCA    96
Val Thr Leu Asn Arg Ile Pro Gly Val Pro Gly Ser Met Pro Asn Ala
            20                  25                  30

TCC                                                                99
Ser
```

( 2 ) INFORMATION FOR SEQ ID NO:6:

( i ) SEQUENCE CHARACTERISTICS:
        ( A ) LENGTH: 33 amino acids
        ( B ) TYPE: amino acid ( D ) TOPOLOGY: linear ( i i ) MOLECULE TYPE: protein ( x i ) SEQUENCE DESCRIPTION: SEQ ID NO:6:

| Leu | Leu | Gln | Trp | Ser | Lys | Asp | Thr | Phe | Ser | Pro | Asp | Glu | His | Phe | Trp |
|---|---|---|---|---|---|---|---|---|---|---|---|---|---|---|---|
| 1 | | | | 5 | | | | | 10 | | | | | 15 | |

| Val | Thr | Leu | Asn | Arg | Ile | Pro | Gly | Val | Pro | Gly | Ser | Met | Pro | Asn | Ala |
|---|---|---|---|---|---|---|---|---|---|---|---|---|---|---|---|
| | | | 20 | | | | | 25 | | | | | 30 | | |

Ser ( 2 ) INFORMATION FOR SEQ ID NO:7:

( i ) SEQUENCE CHARACTERISTICS:
        ( A ) LENGTH: 99 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..99

( x i ) SEQUENCE DESCRIPTION: SEQ ID NO:7:

| TTG | ATG | GAG | TGG | GCA | CAA | GAC | ACA | TAC | AGC | CCT | GAT | GAG | TAT | CTC | TGG | 48 |
|---|---|---|---|---|---|---|---|---|---|---|---|---|---|---|---|---|
| Leu | Met | Glu | Trp | Ala | Gln | Asp | Thr | Tyr | Ser | Pro | Asp | Glu | Tyr | Leu | Trp | |
| 1 | | | | 5 | | | | | 10 | | | | | 15 | | |

| GCC | ACC | ATC | CAA | AGG | ATT | CCT | GAA | GTC | CCG | GGC | TCA | CTC | CCT | AAT | GCC | 96 |
|---|---|---|---|---|---|---|---|---|---|---|---|---|---|---|---|---|
| Ala | Thr | Ile | Gln | Arg | Ile | Pro | Glu | Val | Pro | Gly | Ser | Leu | Pro | Asn | Ala | |
| | | | 20 | | | | | 25 | | | | | 30 | | | |

AGC                                                                                                                         99
Ser ( 2 ) INFORMATION FOR SEQ ID NO:8:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Leu | Met | Glu | Trp | Ala | Gln | Asp | Thr | Tyr | Ser | Pro | Asp | Glu | Tyr | Leu | Trp |
|---|---|---|---|---|---|---|---|---|---|---|---|---|---|---|---|
| 1 | | | | 5 | | | | | 10 | | | | | 15 | |

| Ala | Thr | Ile | Gln | Arg | Ile | Pro | Glu | Val | Pro | Gly | Ser | Leu | Pro | Asn | Ala |
|---|---|---|---|---|---|---|---|---|---|---|---|---|---|---|---|
| | | | 20 | | | | | 25 | | | | | 30 | | |

Ser ( 2 ) INFORMATION FOR SEQ ID NO:9:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..66

( x i ) SEQUENCE DESCRIPTION: SEQ ID NO:9:

| TGT | ATC | TAT | GGA | AAC | GGA | GAC | TTA | AAG | TGG | CTG | GTT | AAT | TCA | CCA | AGC | 48 |
|---|---|---|---|---|---|---|---|---|---|---|---|---|---|---|---|---|

```
Cys Ile Tyr Gly Asn Gly Asp Leu Lys Trp Leu Val Asn Ser Pro Ser
 1               5                  10                  15

CTG TTT GCT AAC AAG TTT                                                        66
Leu Phe Ala Asn Lys Phe
             20
```

( 2 ) INFORMATION FOR SEQ ID NO:10:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Cys Ile Tyr Gly Asn Gly Asp Leu Lys Trp Leu Val Asn Ser Pro Ser
 1               5                  10                  15

Leu Phe Ala Asn Lys Phe
             20
```

( 2 ) INFORMATION FOR SEQ ID NO:11:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..66

( x i ) SEQUENCE DESCRIPTION: SEQ ID NO:11:

```
TGC ATT TTC GGA GCT GGT GAC TTG AAC TGG ATG CTG CGC AAA CAC CAC              48
Cys Ile Phe Gly Ala Gly Asp Leu Asn Trp Met Leu Arg Lys His His
 1               5                  10                  15

TTG TTT GCC AAT AAG TTT                                                        66
Leu Phe Ala Asn Lys Phe
             20
```

( 2 ) INFORMATION FOR SEQ ID NO:12:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Cys Ile Phe Gly Ala Gly Asp Leu Asn Trp Met Leu Arg Lys His His
 1               5                  10                  15

Leu Phe Ala Asn Lys Phe
             20
```

( 2 ) INFORMATION FOR SEQ ID NO:13:

( i ) SEQUENCE CHARACTERISTICS:
        ( A ) LENGTH: 1807 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:

( A ) NAME/KEY: CDS
( B ) LOCATION: 255..1454

( x i ) SEQUENCE DESCRIPTION: SEQ ID NO:13:

| | | | | | | |
|---|---|---|---|---|---|---|
| CTGGGCTTCA | GCAACCTGCC | ACGGGGATTT | AAACAAAGGA | GGTTTGAGAG | AGGCGGGATC | 60 |
| TGGCTGTAAT | ATCGGCACAG | GGACAGAGAC | AGCAGCTGGA | CTCTCGGGAT | GAAACGGAAT | 120 |
| CGATTCCCAG | CGTCTCCAAC | AGGGCAGGAG | TGAGTGGAGT | ATGTTGCAAA | ATAAGAACTC | 180 |
| AGAGAAACGA | GTGAGTTTGG | AAAAAAGACT | TACAGATTTT | GACGGTCTCT | TGACATTTCA | 240 |

```
CCCTTCTTTG  AGGC ATG CCT TTA TCA ATG CGT TAC CTC TTC ATA ATT TCT       290
             Met Pro Leu Ser Met Arg Tyr Leu Phe Ile Ile Ser
              1               5                  10

GTC TCT AGT GTA ATT ATT TTT ATC GTC TTC TCT GTG TTC AAT TTT GGG        338
Val Ser Ser Val Ile Ile Phe Ile Val Phe Ser Val Phe Asn Phe Gly
             15                  20                  25

GGA GAT CCA AGC TTC CAA AGG CTA AAT ATC TCA GAC CCT TTG AGG CTG        386
Gly Asp Pro Ser Phe Gln Arg Leu Asn Ile Ser Asp Pro Leu Arg Leu
         30                  35                  40

ACT CAA GTT TGC ACA TCT TTT ATC AAT GGA AAA ACA CGT TTC CTG TGG        434
Thr Gln Val Cys Thr Ser Phe Ile Asn Gly Lys Thr Arg Phe Leu Trp
 45                  50                  55                  60

AAA AAC AAA CTA ATG ATC CAT GAG AAG TCT TCT TGC AAG GAA TAC TTG        482
Lys Asn Lys Leu Met Ile His Glu Lys Ser Ser Cys Lys Glu Tyr Leu
                 65                  70                  75

ACC CAG AGC CAC TAC ATC ACA GCC CCT TTA TCT AAG GAA GAA GCT GAC        530
Thr Gln Ser His Tyr Ile Thr Ala Pro Leu Ser Lys Glu Glu Ala Asp
             80                  85                  90

TTT CCC TTG GCA TAT ATA ATG GTC ATC CAT CAT CAC TTT GAC ACC TTT        578
Phe Pro Leu Ala Tyr Ile Met Val Ile His His His Phe Asp Thr Phe
         95                 100                 105

GCA AGG CTC TTC AGG GCT ATT TAC ATG CCC CAA AAT ATC TAC TGT GTT        626
Ala Arg Leu Phe Arg Ala Ile Tyr Met Pro Gln Asn Ile Tyr Cys Val
    110                 115                 120

CAT GTG GAT GAA AAA GCA ACA ACT GAA TTT AAA GAT GCG GTA GAG CAA        674
His Val Asp Glu Lys Ala Thr Thr Glu Phe Lys Asp Ala Val Glu Gln
125                 130                 135                 140

CTA TTA AGC TGC TTC CCA AAC GCT TTT CTG GCT TCC AAG ATG GAA CCC        722
Leu Leu Ser Cys Phe Pro Asn Ala Phe Leu Ala Ser Lys Met Glu Pro
                145                 150                 155

GTT GTC TAT GGA GGG ATC TCC AGG CTC CAG GCT GAC CTG AAC TGC ATC        770
Val Val Tyr Gly Gly Ile Ser Arg Leu Gln Ala Asp Leu Asn Cys Ile
            160                 165                 170

AGA GAT CTT TCT GCC TTC GAG GTC TCA TGG AAG TAC GTT ATC AAC ACC        818
Arg Asp Leu Ser Ala Phe Glu Val Ser Trp Lys Tyr Val Ile Asn Thr
        175                 180                 185

TGT GGG CAA GAC TTC CCC CTG AAA ACC AAC AAG GAA ATA GTT CAG TAT        866
Cys Gly Gln Asp Phe Pro Leu Lys Thr Asn Lys Glu Ile Val Gln Tyr
    190                 195                 200

CTG AAA GGA TTT AAA GGT AAA AAT ATC ACC CCA GGG GTG CTG CCC CCA        914
Leu Lys Gly Phe Lys Gly Lys Asn Ile Thr Pro Gly Val Leu Pro Pro
205                 210                 215                 220

GCT CAT GCA ATT GGA CGG ACT AAA TAT GTC CAC CAA GAG CAC CTG GGC        962
Ala His Ala Ile Gly Arg Thr Lys Tyr Val His Gln Glu His Leu Gly
                225                 230                 235

AAA GAG CTT TCC TAT GTG ATA AGA ACA ACA GCG TTG AAA CCG CCT CCC       1010
Lys Glu Leu Ser Tyr Val Ile Arg Thr Thr Ala Leu Lys Pro Pro Pro
            240                 245                 250

CCC CAT AAT CTC ACA ATT TAC TTT GGC TCT GCC TAT GTG GCT CTA TCA       1058
Pro His Asn Leu Thr Ile Tyr Phe Gly Ser Ala Tyr Val Ala Leu Ser
        255                 260                 265
```

-continued

| | | | | | | | | | | | | | | | | |
|---|---|---|---|---|---|---|---|---|---|---|---|---|---|---|---|---|
|AGA|GAG|TTT|GCC|AAC|TTT|GTT|CTG|CAT|GAC|CCA|CGG|GCT|GTT|GAT|TTG|1106|
|Arg|Glu|Phe|Ala|Asn|Phe|Val|Leu|His|Asp|Pro|Arg|Ala|Val|Asp|Leu| |
| |270| | | |275| | | | |280| | | | | | |
|CTC|CAG|TGG|TCC|AAG|GAC|ACT|TTC|AGT|CCT|GAT|GAG|CAT|TTC|TGG|GTG|1154|
|Leu|Gln|Trp|Ser|Lys|Asp|Thr|Phe|Ser|Pro|Asp|Glu|His|Phe|Trp|Val| |
|285| | | | |290| | | | |295| | | | |300| |
|ACA|CTC|AAT|AGG|ATT|CCA|GGT|GTT|CCT|GGC|TCT|ATG|CCA|AAT|GCA|TCC|1202|
|Thr|Leu|Asn|Arg|Ile|Pro|Gly|Val|Pro|Gly|Ser|Met|Pro|Asn|Ala|Ser| |
| | | | |305| | | | |310| | | | |315| | |
|TGG|ACT|GGA|AAC|CTC|AGA|GCT|ATA|AAG|TGG|AGT|GAC|ATG|GAA|GAC|AGA|1250|
|Trp|Thr|Gly|Asn|Leu|Arg|Ala|Ile|Lys|Trp|Ser|Asp|Met|Glu|Asp|Arg| |
| | | |320| | | | |325| | | | |330| | | |
|CAC|GGA|GGC|TGC|CAC|GGC|CAC|TAT|GTA|CAT|GGT|ATT|TGT|ATC|TAT|GGA|1298|
|His|Gly|Gly|Cys|His|Gly|His|Tyr|Val|His|Gly|Ile|Cys|Ile|Tyr|Gly| |
| | |335| | | | |340| | | | |345| | | | |
|AAC|GGA|GAC|TTA|AAG|TGG|CTG|GTT|AAT|TCA|CCA|AGC|CTG|TTT|GCT|AAC|1346|
|Asn|Gly|Asp|Leu|Lys|Trp|Leu|Val|Asn|Ser|Pro|Ser|Leu|Phe|Ala|Asn| |
| |350| | | | |355| | | | |360| | | | | |
|AAG|TTT|GAG|CTT|AAT|ACC|TAC|CCC|CTT|ACT|GTG|GAA|TGC|CTA|GAA|CTG|1394|
|Lys|Phe|Glu|Leu|Asn|Thr|Tyr|Pro|Leu|Thr|Val|Glu|Cys|Leu|Glu|Leu| |
|365| | | | |370| | | | |375| | | | |380| |
|AGG|CAT|CGC|GAA|AGA|ACC|CTC|AAT|CAG|AGT|GAA|ACT|GCG|ATA|CAA|CCC|1442|
|Arg|His|Arg|Glu|Arg|Thr|Leu|Asn|Gln|Ser|Glu|Thr|Ala|Ile|Gln|Pro| |
| | | | |385| | | | |390| | | | |395| | |
|AGC|TGG|TAT|TTT|TGAGCTATTC|ATGAGCTACT|CATGACTGAA|GGGAAACTGC| | | | | | | | |1494|
|Ser|Trp|Tyr|Phe| | | | | | | | | | | | | |
| | | |400| | | | | | | | | | | | | |

AGCTGGGAAG AGGAGCCTGT TTTTGTGAGA GACTTTTGCC TTCGTAATGT TAACCGTTTC 1554

AGGACCACGT TTATAGCTTC AGGACCTGGC TACGTAATTA TACTTAAAAT ATCCACTGGA 1614

CACTGTGAAA TACACTAACA GGATGGCTGG GTAGAGCAAT CTGGGCACTT TGGCCAATTT 1674

TAGTCTTGCT GTTTCTTGAT GCTCACCTCT ATATTAGTTT ATTGTTAGGA TCAATGATAA 1734

ATTAAAATGA CCTCAGATCT TTGCACCAGA TACTCATCAT ATACAAATGT TTAGTAAAA 1794

AAGAGAATTG TAG 1807

( 2 ) INFORMATION FOR SEQ ID NO:14:

( i ) SEQUENCE CHARACTERISTICS:
( A ) LENGTH: 400 amino acids
( B ) TYPE: amino acid
( D ) TOPOLOGY: linear ( i i ) MOLECULE TYPE: protein ( x i ) SEQUENCE DESCRIPTION: SEQ ID NO:14:

| | | | | | | | | | | | | | | |
|---|---|---|---|---|---|---|---|---|---|---|---|---|---|---|
|Met|Pro|Leu|Ser|Met|Arg|Tyr|Leu|Phe|Ile|Ile|Ser|Val|Ser|Val|
|1| | | |5| | | | |10| | | | |15|
|Ile|Ile|Phe|Ile|Val|Phe|Ser|Val|Phe|Asn|Phe|Gly|Gly|Asp|Pro|Ser|
| | | |20| | | | |25| | | | |30| | |
|Phe|Gln|Arg|Leu|Asn|Ile|Ser|Asp|Pro|Leu|Arg|Leu|Thr|Gln|Val|Cys|
| | |35| | | | |40| | | | |45| | | |
|Thr|Ser|Phe|Ile|Asn|Gly|Lys|Thr|Arg|Phe|Leu|Trp|Lys|Asn|Lys|Leu|
| |50| | | | |55| | | | |60| | | | |
|Met|Ile|His|Glu|Lys|Ser|Ser|Cys|Lys|Glu|Tyr|Leu|Thr|Gln|Ser|His|
|65| | | | |70| | | | |75| | | | |80|
|Tyr|Ile|Thr|Ala|Pro|Leu|Ser|Lys|Glu|Glu|Ala|Asp|Phe|Pro|Leu|Ala|
| | | | |85| | | | |90| | | | |95| |
|Tyr|Ile|Met|Val|Ile|His|His|His|Phe|Asp|Thr|Phe|Ala|Arg|Leu|Phe|

-continued

|   |   |   |   |   | 100 |   |   |   |   | 105 |   |   |   | 110 |   |
|---|---|---|---|---|---|---|---|---|---|---|---|---|---|---|---|
| Arg | Ala | Ile<br>115 | Tyr | Met | Pro | Gln | Asn<br>120 | Ile | Tyr | Cys | Val | His<br>125 | Val | Asp | Glu |
| Lys | Ala<br>130 | Thr | Thr | Glu | Phe | Lys<br>135 | Asp | Ala | Val | Glu | Gln<br>140 | Leu | Leu | Ser | Cys |
| Phe<br>145 | Pro | Asn | Ala | Phe | Leu<br>150 | Ala | Ser | Lys | Met | Glu<br>155 | Pro | Val | Val | Tyr | Gly<br>160 |
| Gly | Ile | Ser | Arg | Leu<br>165 | Gln | Ala | Asp | Leu | Asn<br>170 | Cys | Ile | Arg | Asp | Leu<br>175 | Ser |
| Ala | Phe | Glu | Val<br>180 | Ser | Trp | Lys | Tyr | Val<br>185 | Ile | Asn | Thr | Cys | Gly<br>190 | Gln | Asp |
| Phe | Pro | Leu<br>195 | Lys | Thr | Asn | Lys | Glu<br>200 | Ile | Val | Gln | Tyr | Leu<br>205 | Lys | Gly | Phe |
| Lys | Gly<br>210 | Lys | Asn | Ile | Thr | Pro<br>215 | Gly | Val | Leu | Pro | Pro<br>220 | Ala | His | Ala | Ile |
| Gly<br>225 | Arg | Thr | Lys | Tyr | Val<br>230 | His | Gln | Glu | His | Leu<br>235 | Gly | Lys | Glu | Leu | Ser<br>240 |
| Tyr | Val | Ile | Arg | Thr<br>245 | Thr | Ala | Leu | Lys | Pro<br>250 | Pro | Pro | Pro | His<br>255 | Asn | Leu |
| Thr | Ile | Tyr | Phe<br>260 | Gly | Ser | Ala | Tyr | Val<br>265 | Ala | Leu | Ser | Arg | Glu<br>270 | Phe | Ala |
| Asn | Phe | Val<br>275 | Leu | His | Asp | Pro | Arg<br>280 | Ala | Val | Asp | Leu | Leu<br>285 | Gln | Trp | Ser |
| Lys | Asp<br>290 | Thr | Phe | Ser | Pro | Asp<br>295 | Glu | His | Phe | Trp | Val<br>300 | Thr | Leu | Asn | Arg |
| Ile<br>305 | Pro | Gly | Val | Pro | Gly<br>310 | Ser | Met | Pro | Asn | Ala<br>315 | Ser | Trp | Thr | Gly | Asn<br>320 |
| Leu | Arg | Ala | Ile | Lys<br>325 | Trp | Ser | Asp | Met | Glu<br>330 | Asp | Arg | His | Gly | Gly<br>335 | Cys |
| His | Gly | His | Tyr<br>340 | Val | His | Gly | Ile | Cys<br>345 | Ile | Tyr | Gly | Asn | Gly<br>350 | Asp | Leu |
| Lys | Trp | Leu<br>355 | Val | Asn | Ser | Pro | Ser<br>360 | Leu | Phe | Ala | Asn | Lys<br>365 | Phe | Glu | Leu |
| Asn | Thr<br>370 | Tyr | Pro | Leu | Thr | Val<br>375 | Glu | Cys | Leu | Glu | Leu<br>380 | Arg | His | Arg | Glu |
| Arg<br>385 | Thr | Leu | Asn | Gln | Ser<br>390 | Glu | Thr | Ala | Ile | Gln<br>395 | Pro | Ser | Trp | Tyr | Phe<br>400 |

We claim:

1. A nucleic acid molecule selected from the group consisting of:
   a) a nucleotide sequence comprising SEQ ID NO: 1;
   b) a nucleotide sequence complementary to said nucleotide sequence comprising SEQ ID NO: 1; and
   c) a mixture of said nucleotide sequence comprising SEQ ID NO: 1 and said nucleotide sequence complementary to said nucleotide sequence comprising SEQ ID NO: 1, wherein said mixture of nucleotide sequences comprises single stranded nucleic acid molecules or double stranded nucleic acid molecules.

2. A nucleic acid molecule selected from the group consisting of:
   a) a nucleotide sequence comprising SEQ ID NO: 13;
   b) a nucleotide sequence complementary to said nucleotide sequence comprising SEQ ID NO: 13; and
   c) a mixture of said nucleotide sequence comprising SEQ ID NO: 13 and said nucleotide sequence complementary to said nucleotide sequence comprising SEQ ID NO: 13, wherein said mixture of nucleotide sequences comprises single stranded nucleic acid molecules or double stranded nucleic acid molecules.

3. A nucleic acid molecule selected from the group consisting of:
   a) a nucleotide sequence encoding an amino acid sequence comprising SEQ ID NO: 2;
   b) a nucleotide sequence complementary to said nucleotide sequence encoding an amino acid sequence comprising SEQ ID NO: 2; and
   c) a mixture of said nucleotide sequence encoding an amino acid sequence comprising SEQ ID NO: 2 and said nucleotide sequence complementary to said nucleotide sequence encoding an amino acid sequence comprising SEQ ID NO: 2, wherein said mixture of nucleotide sequences comprises single stranded nucleic acid molecules or double stranded nucleic acid molecules.

4. A nucleic acid molecule selected from the group consisting of:

a) a nucleotide sequence encoding an amino acid sequence comprising SEQ ID NO: 14;

b) a nucleotide sequence complementary to said nucleotide sequence encoding an amino acid sequence comprising SEQ ID NO: 14; and c) a mixture of said nucleotide sequence encoding an amino acid sequence comprising SEQ ID NO: 14 and said nucleotide sequence complementary to said nucleotide sequence encoding an amino acid sequence comprising SEQ ID NO: 14, wherein said mixture of nucleotide sequences comprises single stranded nucleic acid molecules or double stranded nucleic acid molecules.

5. A vector containing a nucleic acid molecule comprising a nucleotide sequence selected from the group consisting of:

a) the nucleotide sequence of SEQ ID NO: 1;

b) a nucleotide sequence encoding the amino acid sequence of SEQ ID NO: 2;

c) the nucleotide sequence of SEQ ID NO: 13; and d) a nucleotide sequence encoding the amino acid sequence of SEQ ID NO: 14.

6. The vector of claim 5, wherein the vector is a plasmid.

7. The vector of claim 5, wherein said vector is an expression vector.

8. A host cell containing the vector of claim 5.

9. A process for obtaining a substantially purified soluble active fragment of human IGnT, comprising the steps of:

a. introducing a nucleic acid molecule encoding the soluble active fragment of human IGnT into a suitable host cell, said nucleic acid molecule selected from the group consisting of a nucleic acid molecule comprising the nucleotide sequence of SEQ ID NO: 1 and a nucleic acid molecule comprising a nucleotide sequence encoding SEQ ID NO: 2;

b. expressing the soluble active fragment of human IGnT; and c. substantially purifying the expressed soluble active fragment of human IGnT.

10. A process for obtaining a host cell expressing a recombinant human IGnT or a soluble active fragment thereof, comprising the steps of:

a. introducing a nucleic acid molecule comprising a nucleotide sequence selected from the group consisting of:

1) the nucleotide sequence of SEQ ID NO: 1;

2) a nucleotide sequence encoding the amino acid sequence of SEQ ID NO: 2;

3) the nucleotide sequence of SEQ ID NO: 13; and 4) a nucleotide sequence encoding the amino acid sequence of SEQ ID NO: 14, into a suitable host cell; and b. expressing the recombinant human IGnT or the soluble active fragment thereof in said cell.

* * * * *